US005723699A

United States Patent [19]
Miller et al.

[11] Patent Number: 5,723,699
[45] Date of Patent: Mar. 3, 1998

[54] PURIFICATION PROCESS FOR HEXAFLUOROETHANE PRODUCTS

[75] Inventors: Ralph Newton Miller; Mark Richard Deschere, both of Newark, Del.; Barry Asher Mahler, Glen Mills, Pa.; Olagappan Muthu, Newark, Del.

[73] Assignee: E. I. du Pont de Nemours and Company, Wilmington, Del.

[21] Appl. No.: 789,173

[22] Filed: Jan. 24, 1997

Related U.S. Application Data

[63] Continuation of Ser. No. 455,883, May 31, 1995, abandoned, which is a continuation of Ser. No. 309,376, Sep. 20, 1994.

[51] Int. Cl.⁶ .................................................... C07C 19/08
[52] U.S. Cl. ............................................................. 570/134
[58] Field of Search ........................................ 570/134, 177, 570/178, 179, 180

[56] References Cited

U.S. PATENT DOCUMENTS

| | | | |
|---|---|---|---|
| 4,950,364 | 8/1990 | Wismer | 203/50 |
| 5,258,561 | 11/1993 | Nappa et al. | 570/169 |

FOREIGN PATENT DOCUMENTS

WO93/17988  9/1993  WIPO .

OTHER PUBLICATIONS

A.J. Waytek, The Role Of Fluorocarbon Gases In The Microelectronics Industry, 1986, 331–334.

Blanchard, Wendlinger and Canesson, Heterogeneous Catalytic Reactions Of Chlorofluorocarbons, 1990, 123–128.

W. Schotte, Collection Of Phase Equilibrium Data For Separation Technology, 1980, 432–439.

Harold R. Null, Phase Equilibrium In Process Design, 1970, 124–126.

Stanley M. Walas, Phase Equilibrium In Chemical Engineering, 1985, 165–244.

The Van Nostrand Chemists Dictionary, 1961, p. 56.

*Primary Examiner*—Alan Siegel

[57] ABSTRACT

The disclosure relates to removing impurities from hexafluoroethane ($CF_3CF_3$), also known as Perfluorocarbon 116 (PFC-116) or Fluorocarbon 116 (FC-116), by using azeotropic distillation such that an overhead product consisting essentially of HCl-hexafluoroethane is formed, optionally combined with a phase separation step to break the HCl-hexafluoroethane azeotropic or azeotrope-like composition thereby permitting recovery of substantially pure hexafluoroethane. Unreacted hydrogen fluoride (HF) may be removed from hexafluoroethane during the above azeotropic distillation with HCl or alternatively by an azeotropic distillation wherein an HF-hexafluoroethane azeotropic or azeotrope-like composition exits overhead and substantially pure HF exits in the bottoms stream.

7 Claims, 18 Drawing Sheets

PURIFICATION PROCESS FOR HEXAFLUOROETHANE PRODUCTS

This is a continuation of application Ser. No. 08/455,883 filed May 31, 1995, now abandoned which is a continuation of application Ser. No. 08/309,367, filed Sep. 20, 1994 (pending).

FIELD OF THE INVENTION

The instant invention relates to the field of removing impurities from hexafluoroethane ($CF_3CF_3$), also known as Perfluorocarbon 116 (PFC-116) or Fluorocarbon 116 (FC-116), by using azeotropic distillation such that an overhead product consisting essentially of HCl-hexafluoroethane is formed, optionally combined with a phase separation step to break the HCl-hexafluoroethane azeotropic or azeotrope-like composition thereby permitting recovery of substantially pure hexafluoroethane. Unreacted hydrogen fluoride (HF) may be removed from hexafluoroethane during the above azeotropic distillation with HCl or alternatively by an azeotropic distillation wherein an HF-hexafluoroethane azeotropic or azeotrope-like composition exits overhead and substantially pure HF exits in the bottoms stream.

BACKGROUND OF THE INVENTION

Conventional methods for manufacturing hexafluoroethane typically result in undesired impurities. Hexafluoroethane can be manufactured by fluorinating at least one of trichlorotrifluoroethane, dichlorotetrafluoroethane and/or chloropentafluoroethane. This hexafluoroethane manufacturing method often produces a product stream containing significant amounts of fluorocarbon and acid impurities which are difficult to remove by conventional distillation techniques.

Various gaseous fluorine-containing compounds are utilized to plasma etch silicon-type materials in order to fabricate semiconductor devices, e.g., A. J. Woytek, J. Fluor. Chem. 33, 331–334 (1986); the disclosure of which is hereby incorporated by reference. A major use of hexafluoroethane is as a plasma etchant in semiconductor device fabrication. It interacts with the surface of the integrated circuit wafer, modifying it so as to lay down the electrical pathways and providing for the surface functionalities that define the integrated circuit. As manufacturers are continually trying to increase the number of functionalities packed per unit surface area, the increasing fineness of surface detail in turn requires greater precision and consistency of the effect the etchant has on the wafer substrate. Products of high purity are critical for this application. It has been found that even very small amounts of impurities can result in wide line width and thus less information bits per chip. Moreover, the presence of these impurities, including but not limited to particulates, metals, moisture, and other halocarbons in the plasma etchant, even when present only in the part per million level, increases the defect rate in the production of these higher density integrated circuits. As a result there has been continually increasing market demand for higher and higher purity etchants, and an increasing market value for materials having the required purity. Consequently, identification of the offending impurities and their removal represents a significant aspect of preparing the fluorine-containing compounds for these applications.

CROSS-REFERENCE TO RELATED PATENTS AND PATENT APPLICATIONS

Certain aspects of this invention are related to the disclosure of commonly assigned U.S. patent application Ser. Nos. 08/055,486, 08/208,256 and U.S. Pat. No. 5,258,561, (corresponding to European Patent Application PCT/US94/04301); the entire disclosure of which is hereby incorporated by reference.

SUMMARY OF THE INVENTION

The instant invention solves the problems associated with conventional hexafluoroethane (FC-116) manufacturing methods by providing an azeotropic distillation method for purifying FC-116. As a result, the instant invention provides a high purity FC-116 product that is needed as an etchant in the electronics industry.

In one aspect of the invention, we have found that at least one of chlorotrifluoromethane (CFC-13), trifluoromethane (HFC-23), chlorodifluoromethane (HCFC-22), chloropentafluoroethane (CFC-115), pentafluoroethane (HFC-125), difluoromethane (HFC-32), 1,1,1-trifluoroethane (HFC-143a), 1,1-difluoroethane (HFC-152a), and HF, among others, can be removed from hexafluoroethane by being distilled in the presence of anhydrous HCl; usually, in the presence of an amount of HCl that is sufficient to form an azeotropic or azeotrope-like composition with all of the hexafluoroethane. The instant invention provides a process whereby an HCl-hexafluoroethane azeotropic or azeotrope-like composition, which is substantially free of impurities such as chlorotrifluoromethane, trifluoromethane, chlorodifluoromethane, chloropentafluoroethane, pentafluoroethane, difluoromethane, 1,1,1-trifluoroethane, 1,1-difluoroethane and HF, can be removed as the overhead stream from a distillation column. By "substantially free" of impurities or "substantially pure", it is meant that the stream contains less than about 1.0 wt %, normally less than 0.1 wt %, and most often less than about 10 ppm of undesired impurities, e.g., the instant invention can produce at least about 99.9999 wt % pure PFC-116. These impurities and/or their azeotropes with HCl or HF can be removed from the bottom of the distillation column. This invention can consequently produce PFC-116 that is greater than 99.999% wt. PFC-116 based on the weight of all components contained within, e.g., 99.9999 wt % pure PFC-116 or containing less than about 1 ppm of undesired impurities.

Another aspect of the invention provides a process for breaking the HCl-hexafluoroethane azeotropic or azeotrope-like compositions into their individual components by liquefying and cooling the recovered azeotrope composition, and allowing the cooled composition to separate into HCl-rich and hexafluoroethane-rich layers within a decanter. The latter layer may then be purified by, for example, by azeotropic distillation thereby yielding substantially pure hexafluoroethane. Optionally, the HCl-rich layer may be purified, for example, by azeotropic distillation to produce substantially pure anhydrous HCl.

In another aspect, the invention comprises i) removing a portion of the trifluoromethane (HFC-23) along with the HCl-hexafluoroethane azeotropic or azeotrope-like composition from a first column's overhead stream wherein the remainder of the HFC-23 (with the other impurities) exits in the column's bottom stream, ii), separating the overhead stream within a decanter into HCl-rich and hexafluoroethane-rich layers as previously described, and iii) distilling the hexafluoroethane-rich layer in a second distillation column and recycling a HCl-hexafluoroethane azeotrope composition, which exits from the second distillation column and now contains a portion of the original trifluoromethane, to the first distillation column. The hexafluoroethane exiting from the bottoms of the second distillation column will now be substantially free of trifluoromethane and HCl as well as the other impurities.

In another case, the hexafluoroethane may contain quantities of HCl and optionally at least one of CFC-13, CFC-115, HFC-23, among others. By operating a distillation column under conditions that cause formation of azeotropic or azeotrope-like compositions consisting essentially of HCl and one or more of PFC-116, CFC-13, CFC-115 and HFC-23, such compositions can be removed from the distillation column as an overhead product thereby purifying the hexafluoroethane. The hexafluoroethane can, if desired, be purified further by using the aforementioned methods.

In another case, the hexafluoroethane may contain quantities of HF and optionally one or more of CFC-115, CFC-114, CFC-114a, CFC-113, CFC-113a, CFC-13, HCFC-22, HFC-143a, HFC-125 among Others. By operating a distillation column under conditions that cause formation of azeotropic or azeotrope-like composition consisting essentially of HF and one or more of PFC-116, CFC-115, CFC-114, CFC-114a, CFC-113, CFC-113a, CFC-13, HCFC-22, HFC-143a and HFC-125, such azeotropes can be removed thereby purifying the hexafluoroethane. The hexafluoroethane can, if desired, be purified further by using the aforementioned methods.

In still another case, the hexafluoroethane may contain quantities of at least one of HFC-23, CFC-13, among others. By operating a distillation column under conditions that cause formation of azeotropic or azeotrope-like compositions consisting essentially of FC-116 and one or more of HFC-23 and CFC-13, such azeotropes can be removed as an overhead product thereby purifying the hexafluoroethane. The remaining hexafluoroethane can, if desired, be purified by using the aforementioned methods.

In a further aspect, the invention can provide an improved process for producing hexafluoroethane by fluorinating trichlorotrifluoroethane(s), dichlorotetrafluoroethane(s) and/ or chloropentafluoroethane to produce a hexafluoroethane product stream containing chlorotrifluoromethane and other fluorocarbon impurities. The improved process comprises the steps of removing these impurities from the hexafluoroethane product stream by using the azeotropic distillation processes described above.

The invention also provides a method for separating HF from a mixture comprising HF and hexafluoroethane wherein the HF is present in excess of the HF-hexafluoroethane azeotropic or azeotrope-like composition. The HF is separated by removing the HF-hexafluoroethane composition as an overhead product in a distillation column thereby leaving a purified HF in the bottoms. Further, the invention provides a method for separating a purified HF from a mixture comprising HF and a number of other halogenated compounds, e.g., halocarbons, wherein the HF is present in excess of the HF-halocarbon azeotropic or azeotrope-like composition. In this case, the purified HF is obtained by removing the previously described HF-halocarbon(s) azeotropic or azeotrope-like mixtures as an overhead from a distillation column thereby leaving purified HF in the bottoms.

DETAILED DESCRIPTION

Figure 1:
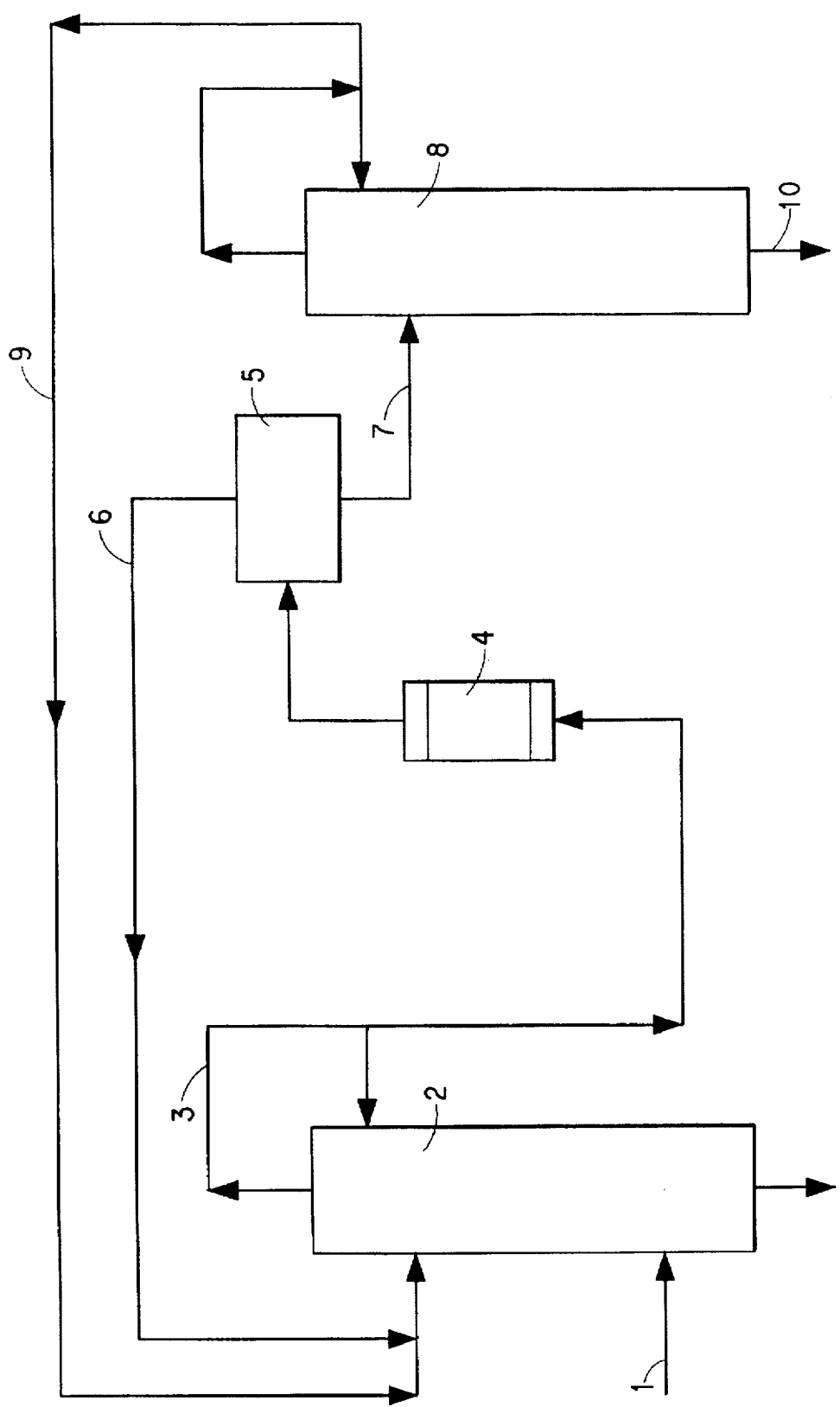
FIG. 1—FIG. 1 is a schematic diagram of a process that can be used for practicing the inventive process.

The present invention relates to a method for purifying hexafluoroethane products containing one or more impurities such as chlorotrifluoromethane, trifluoromethane, chlorodifluoromethane, chloropentafluoroethane, difluoromethane, 1,1,1-trifluoroethane, 1,1-difluoroethane, pentafluoroethane, among others. The present invention also relates to a method for removing acids such as hydrogen fluoride and/or hydrogen chloride, that may be present in the hexafluoroethane, e.g., at least one of hydrogen fluoride and hydrogen chloride that may be present in the hexafluoroethane as a residual reactant or reaction product.

An aspect of the inventive process comprises operating a conventional distillation column under conditions sufficient to form a HCl-hexafluoroethane azeotropic or azeotrope-like composition wherein the composition is substantially free of at least one of the following impurities: chlorotrifluoromethane, trifluoromethane, chlorodifluoromethane, difluoromethane, chloropentafluoroethane, pentafluoroethane, 1,1,1-trifluoroethane, 1,1-difluoroethane, HF, among others. The HCl-hexafluoroethane azeotropic or azeotrope-like composition can be removed as an overhead stream from the top of the distillation column, and the previously identified impurities or their azeotropes with HCl and/or HF can be removed from the bottom of the distillation column.

Another aspect of the invention relates to an optional process for separating an HCl-hexafluoroethane azeotropic or azeotrope-like composition, e.g., the previously discussed azeotropic composition being recovered as an overhead stream, into its individual components. The azeotropic or azeotrope-like composition can be separated into its components by cooling and liquefying the azeotropic composition to below about −50 degrees C. within a conventional decanter thereby allowing the composition to separate into HCl-rich and hexafluoroethane-rich layers.

The hexafluoroethane-rich layer may then be purified by azeotropic distillation in a second distillation column, wherein any remaining HCl can be removed as the HCl-hexafluoroethane azeotropic or azeotrope-like composition in an overhead stream from the top of the second distillation column thereby yielding substantially pure hexafluoroethane from the bottom of the second column. In other words, the relatively small mount of HCl is removed from the hexafluoroethane-rich layer by removing substantially all of the HCl and a portion of the hexafluoroethane as an azeotropic or azeotrope-like composition. The remaining hexafluoroethane is substantially pure.

The HCl-rich layer may then also be purified by azeotropic distillation in a third distillation column, wherein any remaining hexafluoroethane can be removed as the HCl-hexafluoroethane azeotropic or azeotrope-like composition in an overhead stream from the top of the third distillation column thereby yielding substantially pure HCl from the bottom of the third column. In other words, the relatively small amount of hexafluoroethane is removed from the HCl-rich layer by removing substantially all of the hexafluoroethane and a portion of the HCl as an azeotropic or azeotrope-like composition. The remaining HCl is substantially pure.

The instant invention also provides a method for removing certain quantities of trifluoromethane (HFC-23) along with the HCl-hexafluoroethane azeotropic or azeotrope-like composition as an overhead stream in the first distillation column. Any remaining trifluoromethane can be removed with the other impurities in the first column's bottom stream. The overhead product stream can be separated by being introduced into a decanter that causes formation of HCl-rich and hexafluoroethane-rich layers wherein the hexafluoroethane-rich layer includes the portion of trifluoromethane that exited the top of the column. The hexafluoroethane-rich layer can be removed from the decanter and introduced into a second distillation column wherein the overhead product stream contains the HCl-hexafluoroethane azeotropic or azeotrope-like composition and trifluoromethane; both of which can be recycled to the first distillation column. Hexafluoroethane exits from the bottoms of the second distillation column and is normally substantially free of trifluoromethane as well as the impurities that were removed by the first distillation column.

The hexafluoroethane product or feedstock to be purified by this process typically has at least about 90 organic mole percent hexafluoroethane, usually has at least 95 organic mole percent hexafluoroethane, and normally has at least about 99 organic mole percent hexafluoroethane.

The previously described processes can be employed by using an HF-hexafluoroethane azeotropic distillation process. The HF-hexafluoroethane azeotropic distillation process can be employed before, after and/or in some cases as a replacement for the HCl-hexafluoroethane azeotropic distillation process.

Hexafluoroethane products or feedstocks that can be purified by practicing the instant invention may be obtained from any suitable source. One suitable source is a process comprising reacting anhydrous hydrogen fluoride with any one of 1,1,1-trichloro-2,2,2-trifluoroethane (CFC-113a), 1,1,2-trichloro-1,2,2-trifluoroethane (CFC-113), 1,1-dichloro-1,2,2,2-tetrafluoroethane (CFC-114a) or 1,2-dichloro-1,1,2,2-tetrafluoroethane (CFC-114), to form chloropentafluoroethane (CFC-115) and hexafluoroethane (PFC-116), among other compounds. Examples of a suitable process is described in Heterogeneous Catalytic Reactions of Chlorofluoro-Carbons. Blanchard, M.; Wendlinger, L. Canesson, P. Appl. Catal.(1990), 59 (1), 123–8, the disclosure of which is hereby incorporated by reference.

Any unreacted starting materials and CFC-115 may be recycled to the reactor to produce additional quantities of PFC-116. Impurities such as chlorotrifluoromethane (CFC-13), trifluoromethane (HFC-23), chlorodifluoromethane (HCFC-22), difluoromethane (HFC-32), chloropentafluoroethane (CFC-115), 1,1,1-trifluoroethane (HFC-143a), 1,1-difluoroethane (HFC-152a), pentafluoroethane (HFC-125) as well as unreacted HF and byproduct HCl may also be present in the hexafluoroethane product.

Conventional distillation can be used in order to remove a portion of the impurities such as hydrogen chloride, hydrogen fluoride and high-boilers including tars, to produce a hexafluoroethane product which contains at least about 90 organic mol percent hexafluoroethane.

If desired, bulk quantities of impurities in the hexafluoroethane product can also be removed from the hexafluoroethane product by using azeotropic distillation. For example, the impurity concentration can be reduced by passing the hexafluoroethane containing product through a distillation column which is operated under conditions sufficient to permit withdrawing at least one of following azeotropic or azeotrope-like compositions as an overhead product: HCl/PFC-116, HCl/CFC-13, HCl/HFC-23, HCl/CFC-115, PFC-116/HFC-23, PFC-116/CFC-13, PFC-116/HFC-32, HF/PFC-116, HF/CFC-115, HF/CFC-114, HF/CFC-114a, HF/CFC-113, HF/CFC-113a, HF/CFC-13, HF/HCFC-22, HF/HFC-143a, HF/HFC-125, among others. The previously described HCl-hexafluoroethane and/or HF-hexafluoroethane azeotropic distillation processes can then be employed to produce substantially pure hexafluoroethane.

A key aspect of this invention relates to the relative volatilities of hexafluoroethane and each of its impurities versus anhydrous HCl, and to a lesser extent to the relative volatility of hexafluoroethane versus HF. To determine the relative volatility of hexafluoroethane and HCl, for example, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126; the entire disclosure of which is hereby incorporated by reference.

These measurements can reduced to equilibrium vapor and liquid compositions in the PTx cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4th edition, publisher McGraw Hill, written by Reid, Prausnitz and Poling, on pages 241 to 387; and in "Phase Equilibria in Chemical Engineering, published by Butterworth Publishers, 1985, written by Stanley M. Walas, pages 165 to 244; the entire disclosure of which is hereby incorporated for reference.

The behavior of hydrogen fluoride in such systems may also be calculated by using an appropriate hydrogen fluoride association model in conjunction with the aforementioned methods as described by W. Schotte, Ind. Eng. Chem. Process Des. Dev. 1980, 19, pp 432–439; the entire disclosure of which is hereby incorporated by reference.

Without wishing to be bound by any theory or explanation, it is believed that the NRTL equation in conjunction with the other referenced models can sufficiently predict whether or not hexafluoroethane and HCl mixtures and/or the following other mixtures behave in an ideal manner, and can sufficiently predict the relative volatilities of the components in such mixtures.

The results of PTx measurements and the above series of calculations are summarized in Tables 1 and 2 below, giving results for mixtures consisting essentially of PFC-116 with CFC-13 at about −18.55 degrees C. and PFC-116 with HFC-23 at about −45.55 degrees C. respectively.

TABLE 1

Vapor-Liquid Measurements on PFC-116/CFC-13 System at −18.55 Deg C.

| Mole % PFC-116 | | Pressure | Activity Coefficient | | Relative Volatility |
|---|---|---|---|---|---|
| Liquid | Vapor | psia | PFC-116 | CFC-13 | PFC-116/CFC-13 |
| 0.00 | 0.00 | 170.84 | 1.191 | 1.000 | 1.091 |
| 3.78 | 4.06 | 171.58 | 1.174 | 1.000 | 1.077 |
| 9.44 | 9.92 | 172.38 | 1.149 | 1.002 | 1.057 |
| 15.07 | 15.55 | 173.02 | 1.127 | 1.004 | 1.038 |
| 19.97 | 20.32 | 173.34 | 1.110 | 1.008 | 1.022 |
| 25.04 | 25.16 | 173.55 | 1.095 | 1.012 | 1.006 |
| 32.43 | 32.09 | 173.37 | 1.074 | 1.019 | 0.985 |
| 47.97 | 46.50 | 172.27 | 1.041 | 1.041 | 0.943 |
| 57.68 | 55.60 | 170.74 | 1.026 | 1.058 | 0.919 |
| 62.83 | 60.52 | 169.53 | 1.019 | 1.068 | 0.907 |
| 69.05 | 66.59 | 168.12 | 1.013 | 1.081 | 0.893 |
| 74.69 | 72.23 | 166.45 | 1.008 | 1.094 | 0.881 |
| 89.24 | 87.62 | 161.62 | 1.001 | 1.131 | 0.853 |
| 94.78 | 93.87 | 159.48 | 1.000 | 1.146 | 0.843 |
| 100.00 | 100.00 | 157.25 | 1.000 | 1.161 | 0.834 |

The "Mole %" column refers to the quantity of PFC-116 that is in the liquid and vapor portions of the PFC-116/CFC-13 mixture within the PTx Cell.

TABLE 2

Vapor-Liquid Measurements on PFC-116/HFC-23 System at −45.55 Deg C.

| Mole % PFC-116 | | Pressure | Activity Coefficient | | Relative Volatility |
|---|---|---|---|---|---|
| Liquid | Vapor | psia | PFC-116 | HFC-23 | PFC-116/HFC-23 |
| 0.00 | 0.00 | 83.91 | 3.047 | 1.000 | 2.394 |
| 8.25 | 15.18 | 92.69 | 2.523 | 1.008 | 1.992 |
| 15.73 | 23.95 | 97.84 | 2.164 | 1.029 | 1.687 |
| 21.62 | 29.01 | 99.82 | 1.940 | 1.055 | 1.482 |
| 30.92 | 35.13 | 101.62 | 1.664 | 1.115 | 1.210 |
| 46.70 | 43.04 | 102.62 | 1.348 | 1.273 | 0.862 |
| 50.52 | 44.81 | 102.14 | 1.292 | 1.325 | 0.795 |
| 71.32 | 56.11 | 95.77 | 1.089 | 1.731 | 0.514 |
| 73.92 | 57.99 | 93.89 | 1.073 | 1.800 | 0.487 |
| 78.66 | 61.91 | 90.94 | 1.048 | 1.940 | 0.441 |
| 85.16 | 68.84 | 85.59 | 1.023 | 2.167 | 0.385 |
| 86.73 | 70.88 | 84.49 | 1.018 | 2.228 | 0.372 |
| 92.08 | 79.46 | 77.59 | 1.006 | 2.460 | 0.333 |
| 96.04 | 88.11 | 71.99 | 1.002 | 2.656 | 0.306 |
| 100.00 | 100.00 | 64.64 | 1.000 | 2.879 | 0.281 |

The "Mole %" column refers to the quantity of PFC-116 that is in the liquid and vapor portions of the PFC-116/HFC-23 mixture within the PTx Cell.

In Tables 1 and 2 above, the "Relative Volatility" column shows those relative volatilities calculated by using PTx cell pressure which was measured at the temperature indicated on the above Tables. While the relative volatility of PFC-116 in comparison to CFC-13 or HFC-23 at relatively low concentrations is sufficient to permit separating the PFC-116 by conventional methods, the relative volatility becomes 1.0 as 29 mole % PFC-116 is approached at −18.55 degrees C. in the 116/13 case, and becomes 1.0 as 40.0 mole % PFC-116 is approached at −45.55 degrees C. in the 116/23 case. Relative volatilities of 1.0 indicate the presence of an azeotropic or azeotrope-like composition, that renders separating the components of such compositions impractical by using conventional distillation, or necessitates employing an extremely large and expensive distillation column for their separation. The presence of an azeotropic or azeotrope-like composition will also be indicated where, at a given temperature, the PTx cell pressure of specific compositions of mixture of the components is greater than the pressure of other compositions of the same components and of the individual components by themselves, where the azeotropic or azeotrope-like composition is that of the cell vapor space in the maximum pressure region.

Similar to the above examples and discussion, azeotropic or azeotrope-like compositions have been discovered between PFC-116 and relatively small amounts of certain halocarbon impurities, e.g., PFC-116 and HFC-32. Vapor-liquid equilibrium tangent pinches have been discovered between PFC-116 and relatively small amounts of certain other halocarbon impurities, e.g., PFC-116 and HFC-143a, and PFC-116 and HFC-152a. The presence of such impurities in the PFC-116 product are barriers to obtaining substantially pure PFC-116 in high yield.

We have similarly found that azeotropic or azeotrope-like compositions exist between PFC-116 and HCl at a variety of temperatures and pressures. The result of PTx measurements and the above series of calculations for mixtures of PFC-116, CFC-13 and HFC-23 with HCl at about −20 degrees C. are summarized in Tables 3 through 5.

TABLE 3

Vapor-Liquid Measurements on HCl/PFC-116 Binary Mixture at −20.56 Degrees C.

| Mole % HCl | | Pressure | Activity Coefficient | | Relative Volatility |
|---|---|---|---|---|---|
| Liquid | Vapor | psia | HCl | PFC-116 | PFC-116/HCl |
| 100.00 | 100.00 | 211.3 | 1.000 | 14.019 | 8.74 |
| 91.92 | 70.20 | 298.6 | 1.030 | 6.616 | 4.83 |
| 72.61 | 63.65 | 318.0 | 1.266 | 2.395 | 1.514 |
| 58.82 | 62.41 | 319.1 | 1.539 | 1.638 | 0.860 |
| 44.07 | 59.07 | 311.7 | 1.937 | 1.281 | 0.546 |
| 26.78 | 50.52 | 284.7 | 2.602 | 1.087 | 0.358 |
| 4.16 | 16.33 | 181.7 | 4.045 | 1.002 | 0.222 |
| 0.00 | 0.00 | 149.9 | 4.428 | 1.000 | 0.204 |

The "Mole %" column refers to the quantity of HCl that is in the liquid and vapor portions of the HCl/PFC-116 mixture within the PTx Cell.

Table 3 shows the presence of an HCl/PFC-116 azeotropic composition consisting essentially of about 62% HCl and 38% PFC-116 at −20.56 degrees C., with a vapor pressure of about 319 psia.

TABLE 4

Vapor-Liquid Measurements on HCl/CFC-13 Binary Mixture at −20 Degrees C.

| Mole % HCl | | Pressure | Activity Coefficient | | Relative Volatility |
|---|---|---|---|---|---|
| Liquid | Vapor | psia | HCl | CFC-13 | HCl/CFC-13 |
| 100.00 | 100.00 | 215.15 | 1.000 | 5.152 | 0.291 |
| 92.33 | 82.39 | 250.10 | 1.014 | 3.632 | 0.389 |
| 78.79 | 69.80 | 271.40 | 1.094 | 2.290 | 0.622 |
| 69.81 | 65.47 | 276.28 | 1.182 | 1.830 | 0.820 |
| 61.32 | 62.18 | 277.29 | 1.289 | 1.550 | 1.037 |
| 50.00 | 57.77 | 274.80 | 1.472 | 1.311 | 1.368 |
| 35.83 | 50.70 | 263.18 | 1.777 | 1.137 | 1.842 |
| 8.52 | 21.33 | 201.93 | 2.698 | 1.007 | 2.912 |
| 0.00 | 0.00 | 164.41 | 3.117 | 1.000 | 3.285 |

The "Mole %" column refers to the quantity of HCl that is in the liquid and vapor portions of the HCl/CFC-13 mixture within the PTx Cell.

Table 4 shows the presence of an HCl/CFC-13 azeotropic composition consisting essentially of about 62% HCl and 38% CFC-13 at −20 degrees C., with a vapor pressure of about 277 psia.

TABLE 5

Vapor-Liquid Measurements on the HCl/HFC-23 Binary Mixture at −20 Degrees C.

| Mole % HCl | | Pressure | Activity Coefficient | | Relative Volatility |
|---|---|---|---|---|---|
| Liquid | Vapor | psia | HCl | HFC-23 | HFC-23/HCl |
| 100.00 | 100.00 | 215.47 | 1.000 | 2.671 | 2.321 |
| 90.05 | 83.12 | 241.00 | 1.013 | 2.073 | 1.838 |
| 71.91 | 66.78 | 259.26 | 1.093 | 1.491 | 1.274 |
| 65.75 | 62.68 | 262.28 | 1.134 | 1.375 | 1.143 |
| 60.99 | 59.66 | 263.29 | 1.170 | 1.302 | 1.057 |
| 56.57 | 56.90 | 263.29 | 1.207 | 1.246 | 0.987 |
| 52.33 | 54.22 | 262.58 | 1.245 | 1.200 | 0.927 |
| 29.30 | 37.39 | 250.32 | 1.506 | 1.050 | 0.694 |
| 8.84 | 14.56 | 221.34 | 1.812 | 1.004 | 0.569 |
| 0.00 | 0.00 | 202.23 | 1.968 | 1.000 | 0.529 |

The "Mole %" column refers to the quantity of HCl that is in the liquid and vapor portions of the HCl/HFC-23 mixture within the PTx Cell.

Table 5 shows the presence of an HCl/HFC-23 azeotropic composition consisting essentially of about 57% HCl and 43% HFC-23 at −20 degrees C., with a vapor pressure of about 263 psia.

Hydrogen fluoride may also be present in the PFC-116 product or feedstock by virtue of being a residual reactant from the PFC-116 manufacturing process. Tables 6 and 7 list vapor-liquid equilibrium data for PFC-116 with HF and CFC-13 with HF, each pair at a temperature of about −20 degrees C.

TABLE 6

Vapor-Liquid Measurements on the HF/PFC-116 Binary Mixture at −20 Degrees C.

| Mole % HF | | Pressure | Activity Coefficient | |
|---|---|---|---|---|
| Liquid | Vapor | psia | HF | PFC-116 |
| 100.00 | 100.00 | 2.8 | 1.000 | 42.16 |
| 98.73 | 17.83 | 54.8 | 1.002 | 32.87 |
| 93.95 | 8.29 | 145.1 | 1.029 | 15.60 |
| 92.49 | 7.96 | 154.0 | 1.043 | 13.04 |
| 2.37 | 3.08 | 152.4 | 33.44 | 1.006 |
| 1.41 | 1.04 | 153.3 | 41.09 | 1.002 |
| 0.00 | 0.00 | 151.5 | 57.63 | 1.000 |

Table 6 shows the presence of an HF/PFC-116 azeotropic composition at a temperature of about −20 degrees C. with a vapor pressure of about 154 psia, as indicated by mixtures of HF and PFC-116 having a higher vapor pressure than either pure component at this temperature, with the composition of the vapor in the maximum pressure region being that of the azeotrope. Samples of the vapor and NRTL calculations indicate that the azeotropic or azeotrope-like composition consists essentially of about 5.6 mole % HF and 94.4 mole % PFC-116. It is important to note that azeotropic and azeotrope-like compositions consisting essentially of HF and PFC-116 are found at a variety of temperatures and pressures. For example, at a temperature of about −40 degrees C., the HF/PFC-116 azeotrope consists essentially of about 5.4 mole percent HF and 94.6 mole percent PFC-116 and a vapor pressure of about 79.6 psia, whereas at about 0 degrees C., the azeotrope has a composition consisting essentially of about 11 mole percent HF and 89 mole percent PFC-116 and a vapor pressure of about 273 psia. Consequently, operating a distillation column at different temperatures and pressures may alter such HF/PFC-116 azeotropic or azeotrope-like compositions. Such azeotropic or azeotrope-like compositions, however, differ only slightly in composition and vapor pressure from pure PFC-116 thereby rendering it virtually impossible to recover substantially pure PFC-116 from PFC-116 and HF mixtures.

Amounts of HF in excess of the HF/PFC-116 azeotropic composition may be partially separated from PFC-116/HF mixtures by using a distillation column wherein purified HF exits the bottoms of the distillation column, and the HF/PFC-116 azeotropic or azeotrope-like composition exits the distillation column as an overhead product. However, in such circumstances a method is still required to separate the remaining HF from the PFC-116/HF azeotrope.

Other conventional methods for separating HF and PFC-116 are expensive and impractical. For example, the HF may be removed from PFC-116 by contacting the PFC-116/HF mixture with water, the HF being preferentially absorbed into the water solution typically producing an aqueous HF solution as a by-product.

An azeotropic or azeotrope-like composition can also form between HF and CFC-13. The result of PTx measurements for mixtures of HF and CFC-13 are shown in Table 7.

TABLE 7

Vapor-Liquid Measurements on the HF/CFC-13 Binary Mixture at −20 Degrees C.

| Mole % HF | | Pressure | Activity Coefficient | |
|---|---|---|---|---|
| Liquid | Vapor | psia | HF | CFC-13 |
| 100.00 | 100.00 | 2.8 | 1.000 | 30.73 |
| 96.75 | 10.13 | 96.7 | 1.007 | 19.29 |
| 77.73 | 5.72 | 165.0 | 1.221 | 4.37 |
| 75.94 | 5.74 | 165.6 | 1.251 | 4.04 |
| 3.68 | 9.01 | 166.4 | 28.11 | 1.015 |
| 1.94 | 2.24 | 166.3 | 40.42 | 1.005 |
| 1.91 | 2.16 | 165.7 | 40.68 | 1.004 |
| 0.00 | 0.00 | 164.6 | 65.28 | 1.000 |

Table 7 shows the presence of an HF/CFC-13 azeotropic composition at a temperature of about −20 degrees C. with a vapor pressure of about 166 psia, as indicated by mixtures of HF and CFC-13 having a higher vapor pressure than either pure component at this temperature, wherein the composition of the vapor in the maximum pressure region corresponds to the azeotrope. Samples of the vapor and NRTL calculations indicate that the azeotropic or azeotrope-like composition was about 6.0 mole % HF and 94.0 mole % PFC-116 at this temperature.

Similar to the above discussion, azeotropic or azeotrope-like compositions have been discovered between HF and certain other potential process and product stream components, e.g., HF and CFC-115, HF and CFC-114, HF and CFC-114a, HF and CFC-113, HF and CFC-113a, HF and HCFC-22, HF and HFC-125, HF and HFC-143a, among others.

A comparison of the above azeotropes indicates that the HCl/PFC-116 azeotropic or azeotrope-like compositions possess a relatively higher vapor pressure, i.e., the azeotropic compositions are more volatile, than any of the previously tabulated azeotropes at a given temperature. For example, FIGS. 2–18, which are discussed below in greater detail, show the variation in vapor pressure as a function of liquid composition for various binary mixtures, such as those consisting essentially of HCl, HF, PFC-116, HFC-23, and CFC-13. These Figures illustrate the surprising and unexpected differences in vapor pressure found among the PFC-116/HCl azeotropic or azeotrope-like compositions in comparison to the previously identified impurities and azeotropic or azeotrope-like compositions thereof. The present invention utilizes these differences in vapor pressure to purify PFC-116 in an efficient and economical manner. Such differences in vapor pressure permit purifying a hexafluoroethane feedstock or product that contains a wide range of impurities. Depending upon the characteristics of the azeotropic or azeotrope-like impurity composition, these compositions may be recovered as a useful product.

For essentially complete recovery of substantially pure PFC-116 from the feedstock being supplied to the distillation column, the amount of HCl in the distillation column should preferably be sufficient to form an azeotropic or azeotrope-like composition with the PFC-116. Given the relatively high volatility of the PFC-116/HCl azeotropic or azeotrope-like compositions, the PFC-116/HCl azeotropes are recovered from the distillation column as an overhead product. If the amount of HCl is insufficient, the non-azeotroped portion of the PFC-116 may exit the distillation column either with the overhead stream or the bottoms stream or both, depending upon distillation conditions. If the amount of HCl present in the distillation column is in excess of the quantity sufficient to form the PFC-116/HCl azeotropes, the excess HCl will exit the bottom of the column along with other impurities and/or their azeotropes.

The specific conditions that can be used for practicing of the invention depend upon a number of parameters such as the diameter of the distillation column, the location of feed points, the number of separation stages in the column, the reflux ratio used, among other parameters. In addition to the hexafluoroethane product or feedstock to be purified, recycle streams from other points in the overall purification process may be fed to the distillation column, preferably at a feed point most nearly matching the composition flowing past that point in the column. The operating pressure of the distillation system may range from about 15 to 350 psia, normally about 50 to 350 psia. Typically, an increase in the reflux ratio results in an increase in the purity of the HCl/PFC-116 azeotrope, but generally the reflux ratio ranges from 1/1 to about 20/1, normally 5/1 to 10/1. The temperature of the condenser, which is located adjacent to the top of the column, is normally sufficient to substantially fully condense the HCl/PFC-116 azeotrope exiting the top of the column, e.g., about −60 deg C. to about 10 deg C., at about 80.6 to about 681 psia respectively.

Normally, it is desirable that the HCl/PFC-116 azeotropic or azeotrope-like compositions are separated into their components so that substantially pure anhydrous HCl and PFC-116 can be marketed individually. While such separation could be achieved by extracting the HCl with water, this would require drying the purified PFC-116 to remove even traces of water. More importantly, water extraction would generate an aqueous HCl stream which has a lower market value than anhydrous HCl.

We have discovered that HCl/PFC-116 azeotropic or azeotrope-like compositions may be separated into an acid-rich layer or phase and organic-rich layer or phase by cooling the compositions within a commercially available decanter to a temperature below about −50 degrees C., with the separation efficiency increasing with lower temperatures. The separated layers can then be decanted. The composition of the acid-rich and organic-rich layers is determined primarily by the temperature to which the azeotrope composition was cooled.

The effects of temperature upon the azeotrope composition during decantation were measured. Azeotropic or azeotrope-like compositions of HCl and PFC-116 were added to a stirred pressurized cell. The stirring was then stopped, thereby allowing the mixture to achieve equilibrium at a given temperature. When the mixture had separated into two phases, samples were withdrawn from each separated layer for analysis. Samples of the vapor space within the pressurized cell were also taken in order to provide more accurate data, where the vapor space composition represents the azeotrope composition at that temperature. Tests showed substantially only a single liquid phase was present at a temperature of about −40 degrees C. At about −50 degrees C. and −60 degrees C., two liquid phases formed, with the results tabulated in Table 8 below.

TABLE 8

Vapor-Liquid-Liquid Equilibrium Measurements on the HCl/PFC-116 System

| | Mole Fraction of HCl | |
|---|---|---|
| | −50 degrees C. | −60 degrees C. |
| Lower liquid (PFC-116-rich layer) | 0.5080 | 0.3029 |
| Upper liquid (HCl-rich layer) | 0.8929 | 0.9502 |
| Vapor (azeotrope composition) | 0.6182 | 0.6199 |
| Pressure, psia | 123.4 | 83.6 |

Table 8 shows that there is a substantial difference between the compositions of the two liquid layers, with the efficiency and degree of HCl/PFC-116 separation increasing as the temperature is lowered. In addition, there is a substantial difference among the composition of each of the liquid phases in comparison to the original azeotropic composition. The PFC-116-rich liquid layer can be withdrawn from the pressurized cell, which functions as a decanter, and separated further by being supplied to a distillation column wherein HCl can be distilled overhead as HCl/PFC-116 azeotropic or azeotrope-like compositions, leaving substantially pure PFC-116 recovered from the column bottoms. The substantially pure PFC-116 may then be given a final purification to remove trace impurities by being passed through ion exchange beds or other known means to achieve even higher purity. The HCl/PFC-116 azeotropic or azeotrope-like compositions distilled overhead may be recycled to either the first distillation column or a decanter.

Similarly, the HCl-rich liquid layer can be withdrawn from the pressurized cell (decanter) and separated further by using a distillation column to distill azeotropic or azeotrope-like HCl/PFC-116 compositions overhead thereby leaving substantially pure anhydrous HCl recovered from the column bottoms, e.g., the anhydrous HCl is a valued product for a variety of food and pharmaceutical applications. When HCl is present in excess of the amount required to form low boiling azeotropes with organic components, such azeotropes are useful in that they can be used for removing the organic components by distilling the HCl/organic azeotropic or azeotrope-like compositions overhead thereby leaving substantially pure HCl. The HCl containing azeotropic or azeotrope-like compositions that can be formed consist essentially of one or more of the following mixtures: HCl and PFC-116, HCl and CFC-13, HCl and HFC-23, HCl and CFC-115, among others.

In some cases, the HCl-rich layer can alternately be withdrawn from the decanter and recycled to the first distillation column; e.g., the HCl within the HCl-rich layer can be employed to form the PFC-116/HCl azeotropic or azeotrope-like compositions in the first distillation column. In other words, the acid-rich layer withdrawn from the decanter would in turn become a component of the azeotropic or azeotrope-like compositions which are recovered from the first distillation column as an overhead product. Any excess or remaining HCl would exit the bottom of the first column with the organic impurities.

The liquid-liquid decantation temperature is essentially an economic decision, wherein the higher degree of separation between the PFC-116 and HCl which is achieved at increasingly lower temperatures must be balanced against the higher cost of increasingly lower temperature refrigeration.

Figure 2:
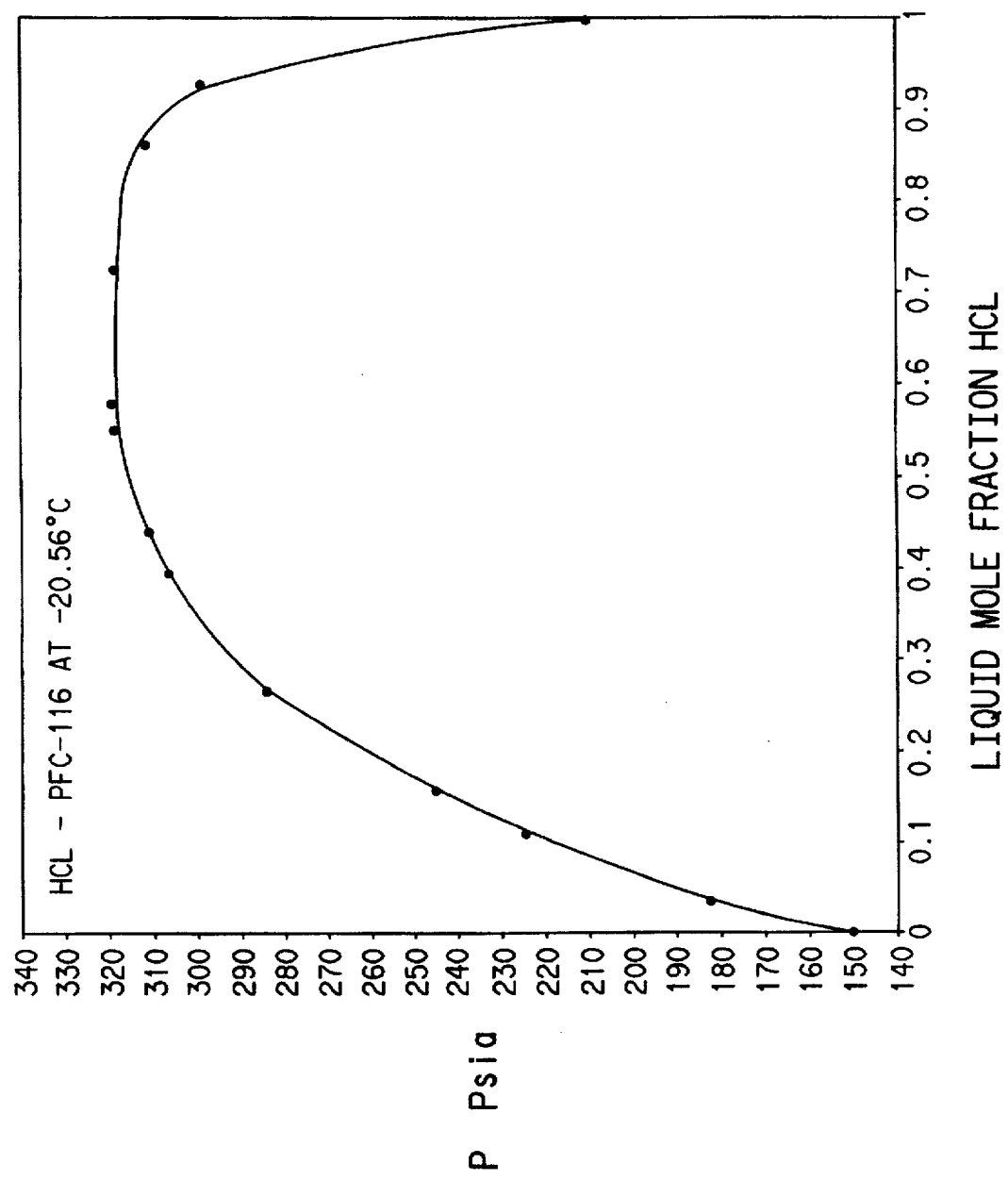
FIG. 2—FIG. 2 is a graphical representation of azeotropic and azeotrope-like compositions consisting essentially of HCl and PFC-116 at a temperature of about −20.56 deg C.
Figure 4:
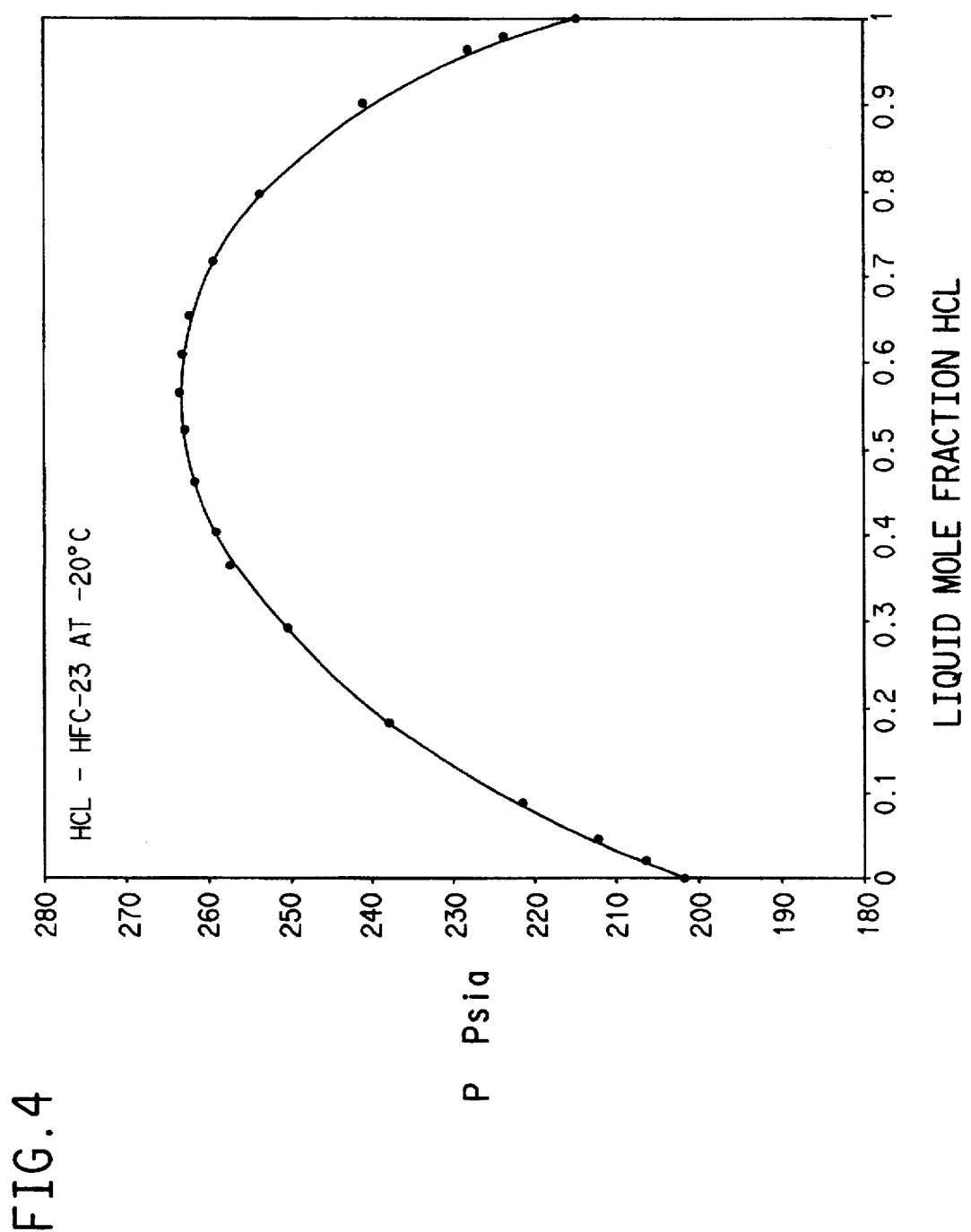
FIG. 4—FIG. 4 is a graphical representation of azeotropic and azeotrope-like compositions consisting essentially of HCl and HFC-23 at a temperature of about −20 deg C.

With respect to a mixture containing HCl, PFC-116, and at least HFC-23, although FIG. 2 and FIG. 4 show a substantial difference among the vapor pressures of the PFC-116/HCl azeotropic or azeotrope-like compositions and the HFC-23 /HCl azeotrope, further tests have indicated that this difference is essentially nullified when the amount of HFC-23 remaining in the PFC-116 product approaches zero because of the activity coefficients at this low concentration. That is, while it is possible to somewhat separate the PFC-116/HCl and HFC-23 /HCl azeotropes by distillation, it is not possible to remove substantially all of the HFC-23 from PFC-116 in a single distillation column. This difficulty can be overcome by increasing the concentration of HFC-23 by recycling any HFC-23, which exits the distillation column with the PFC-116, back into the distillation column until the HFC-23 concentration is sufficient to permit separation by azeotropic distillation. For example, the overhead stream containing the PFC-116/HCl azeotropic or azeotrope-like compositions, and the remainder of the HFC-23 or azeotropes thereof can be cooled and fed to a decanter to break the recovered overhead stream into its individual components, e.g., a PFC-116 rich phase or layer. The PFC-116-rich phase may then be transported to a second distillation column where the HCl/116 and HCl/23 azeotropes may be distilled overhead thereby producing substantially pure PFC-116 out the column bottoms. This distillate may then be fed back to the first column, thereby producing the desired effect of increasing the HFC-23 concentration in that column.

One system that can be used for practicing the instant invention is shown by the schematic diagram in FIG. 1. Referring now to FIG. 1, a hexafluoroethane product or feedstock is supplied by conduit 1 containing PFC-116, HCl and at least one member selected from the group consisting of chlorotrifluoromethane, trifluoromethane, chlorodifluoromethane, chloropentafluoroethane, pentafluoroethane, 1,1,1-trifluoroethane, 1,1-difluoroethane, HF, among others, is introduced to distillation column 2. An anhydrous HCl product that contains other impurities is removed from the bottom of column 2. An HCl/PFC-116 azeotropic or azeotrope-like composition is removed under reflux from column 2 as an overhead product. At least a portion of the HCl/PFC-116 containing stream can be returned to the top of the column as condensed reflux. The ratio of condensed material, which is returned to the column, to the amount of material removed from the column is commonly referred to as the "reflux ratio". The material exiting the top of the column that is not refluxed may then be transported via conduit 3 to a commercially available prechiller 4 that is operated at a temperature of about −50 to −60 deg. C. The chilled composition is supplied to a commercially available decanter 5. The decanter 5 is operated at a temperature less than −50 deg. C., normally at least −50 to −60 deg C., thereby causing the azeotropic composition to be separated into two liquid layers or phases. The lower layer comprises a PFC-116-rich phase and the top layer comprises a HCl-rich phase. While the top layer is HCl-rich, a relatively small quantity of PFC-116 can be present in this layer. The HCl-rich layer is withdrawn from decanter 5 and recycled via conduit 6 to column 2. The recycled HCl-rich layer becomes a source of HCl that is employed to form additional HCl/PFC-116 azeotropic or azeotrope-like compositions in column 2. The PFC-116-rich layer is withdrawn from the bottom of decanter 5 and supplied via conduit 7 to a second distillation column 8. An overhead product stream containing the HCl/PFC-116 azeotropic or azeotrope-like composition is removed, under reflux, from column 8, and recycled via conduit 9 to the first distillation column 2. Similar to the HCl/PFC-116 compositions supplied via conduit 6, the HCl/PFC-116 azeotropic or azeotrope-like compositions in conduit 9 also becomes a source of HCl to form additional quantities of the HCl/PFC-116 azeotropic or azeotrope-like compositions formed in column 2. A substantially pure PFC-116 product exits the bottom 10 of column 8.

While the best results are normally obtained by operating the inventive process under conditions that maximize formation of the HCl/PFC-116 azeotropic or azeotrope-like compositions and minimize formation of halocarbon/halocarbon azeotropic or azeotrope-like compositions, such halocarbon/halocarbon azeotropic or azeotrope-like compositions may be used to purify PFC-116 and/or obtain useful products. In the latter case, the halocarbon/halocarbon azeotropic or azeotrope like compositions can be employed as a pre-purification step for removing relatively large or bulk quantities of impurities from the hexafluoroethane product that in turn can be processed in accordance with the instant invention. The halocarbon/halocarbon azeotropic or azeotrope-like compositions that can be formed consist essentially of one or more of the following mixtures: PFC-116 and CFC-13; PFC-116 and HFC-23; PFC-116 and HFC-32; among others.

It is desirable to recycle any HF, which is recovered by practicing the invention, for reuse as a reactant to manufacture PFC-116. However, it is generally undesirable to simultaneously recycle trace-organics with the HF because such organics tend to become concentrated in the PFC-116 product stream. While the best results are normally obtained by operating the inventive process at process conditions that minimize formation of HF-containing azeotropic or azeotrope-like compositions, such compositions may be used to purify recovered HF, as a PFC-116 pre-purification step and/or to recover a useful product. The HF-containing azeotropic or azeotrope-like compositions that can be formed consist essentially of one or more of the following mixtures: HF and PFC-116, HF and CFC-13, HF and HCFC-22, HF and CFC-113, HF and CFC-113a, HF and CFC-114, HF and CFC-114a, HF and CFC-115, HF and HFC-125, HF and HFC-143a, among others. Such HF-containing azeotropic or azeotrope-like compositions may be used to separate HF from the other components, when, for example, PFC-116 is produced by the reaction of HF with CFC-113, CFC-113a, CFC-114 and/or CFC-114a.

Whenever used in the specification and appended claims the terms below are intended to have the following definitions.

By "azeotrope" or "azeotropic" composition is meant a constant boiling liquid admixture of two or more substances that behave as a single substance. One way to characterize an azeotropic composition or mixture is that the vapor produced by partial evaporation or distillation of the liquid has the same composition as the liquid from which it was evaporated or distilled, e.g., the admixture distills/refluxes without compositional change. Constant boiling compositions are characterized as azeotropic because they exhibit either a maximum or minimum boiling point, as compared with that of the non-azeotropic mixtures of the same components. An azeotropic composition can also be characterized as the maximum or minimum vapor pressure for a mixture at a given temperature when plotted as a function of liquid mole fraction.

By "azeotrope-like" composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same compositions as the liquid from which it was evaporated or distilled, e.g., the admixture distills/refluxes without substantial compositional change. An azeotrope-like composition can also be characterized by the area, which is shown by plotting vapor pressure at given temperature as a function of liquid mole fraction, that is adjacent to the maximum or minimum vapor pressure.

Typically, a composition is azeotrope-like, if, after about 50 weight % of the composition is removed such as by evaporation or boiling off, the change between the original composition and the composition remaining is less than about 6% and normally less than about 3% relative to the original composition.

By "effective" amount is intended to refer to the amount of each component of the inventive compositions which, when combined, results in the formation of an azeotropic or azeotrope-like composition. This definition includes the amounts of each component, which amounts may vary depending on the pressure applied to the composition so long as the azeotropic or azeotrope-like compositions continue to exist at the different pressures, but with possible different boiling points. Effective amount also includes the amounts, such as may be expressed in weight percentages, of each component of the compositions of the instant invention which form azeotropic or azeotrope-like compositions at temperatures or pressures other than described herein. Therefore, included in this invention are azeotropic or azeotrope-like compositions consisting essentially of effective amounts of at least one of PFC-116 and HCl, of PFC-116 and at least one fluorinated molecule, of HF and at least one fluorinated molecule, of HCl and at least one fluorinated molecule such that after about 50 weight percent of an original composition is evaporated or boiled off to produce a remaining composition, the change between the original composition and the remaining composition is typically no more than about 6% and normally no more than about 3% or less relative to the original composition.

It is possible to characterize, in effect, a constant boiling admixture which may appear under many guises, depending upon the conditions chosen, by several criteria:

* The composition can be defined as an azeotrope of PFC-116 ("A") and HCl ("B"), or of PFC-116 ("C") and a Fluorinated Halocarbon ("D"), or of HF ("E")and a Fluorinated Halocarbon ("F"), or of HCl ("G") and a Fluorinated Halocarbon ("H") among others, because the term "azeotrope" is at once both definitive and limitative, and requires effective amounts of A,B(or C,D or E,F or G,H) for this unique composition of matter which can be a constant boiling composition.

* It is well known by those skilled in the art, that, at different pressures, the composition of a given azeotrope will vary at least to a degree, and changes in pressure will also change, at least to some degree, the boiling point temperature. Thus, an azeotrope of PFC-116 ("A") and HCl ("B"), or PFC-116 ("C") and a Fluorinated Halocarbon ("D"), or of HF ("E") and a Fluorinated Halocarbon ("F"), or of HCl ("G") and a Fluorinated Halocarbon ("H") among others, represents a unique type of relationship but with a variable composition which depends on temperature and/or pressure. Therefore, compositional ranges, rather than fixed compositions, are often used to define azeotropes.

* The composition can be defined as a particular weight percent relationship or mole percent relationship of PFC-116("A") and HCl ("B"), or PFC-116 ("C") and a Fluorinated Halocarbon ("D"), or of HF ("E") and a Fluorinated Halocarbon ("F"), or of HCl ("G") and a Fluorinated Halocarbon ("H") among others, while recognizing that such specific values point out only one particular relationship and that in actuality, a series of such relationships, presented by A,B (or C,D or E,F or G,H) actually exist for a given azeotrope, varied by the influence of pressure.

* An azeotrope of PFC-116 ("A") and HCl ("B") or of PFC-116 ("C") and a Fluorinated Halocarbon ("CD") or of HF ("E") and a Fluorinated Halocarbon ("F"), or of HCl ("G") and a Fluorinated Halocarbon ("H") among others, can be characterized by defining the compositions as an azeotrope characterized by a boiling point at a given pressure, thus given identifying characteristics without unduly limiting the scope of the invention by a specific numerical composition, which is limited by and is only as accurate as the analytical equipment available.

The azeotrope or azeotrope-like compositions of the present invention may be formed by operating a conventional distillation apparatus, when practicing the inventive distillation method, and by combining effective amounts of the components by any convenient method including mixing, combining, among others.

Recovered PFC-116, HCl, and HF can be purified simultaneously or individually by using the aforementioned azeotropic and azeotrope-like compositions in a process that comprises forming these azeotropic and azeotrope-like compositions within a conventional distillation column. For example, the conventional distillation column can be operated at a temperature and pressure that causes an azeotropic or azeotrope-like composition, which contains a desirable compound, to form thereby permitting removal of the composition, e.g., the impurities remain in the column. Alternatively, the distillation column can operated under conditions that cause an azeotropic or azeotrope-like composition to be formed with an impurity wherein the impurity containing composition is removed by distillation. Depending upon whether the azeotropic or azeotrope-like composition has a maximum or minimum boiling point, the composition will be collected, respectively, in the bottoms or as an overhead product. For example, when the quantity of PFC-116 is relatively large in comparison to undesired impurities, the PFC-116 can be purified by introducing the PFC-116 to a distillation column wherein one or more azeotropic or azeotrope-like composition consisting essentially of, for example, HCl/PFC-116, PFC-116/CFC-13, PFC-116/HFC-23 can be collected overhead as an overhead product in a distillation column thereby leaving substantially pure PFC-116 as a bottoms product.

A key aspect of the invention relates to recovering substantially pure PFC-116. In many cases, the PFC-116 possesses a purity that was heretofore impossible to achieve. The instant invention permits obtaining PFC-116 that is at least 99.999 pure on a weight percent basis whereas commercially available PFC-116 is typically only 99.99 wt % pure, e.g., the instant invention can produce 99.9999 wt % pure PFC-116. Such a purity is desirable for use in electronic industries as an etchant, e.g., in a plasma environment. Even very small amounts of impurity in a plasma etchant are believe to be undesirable, e.g., the market value of the etchant is related to its purity. Consequently, the instant invention provides a high purity PFC-116 product that solves the problems associated with commercially available PFC-116.

The following Examples are provided to illustrate certain aspects of the present invention; but not limit the scope of the appended claims. Parts per million (ppm) are by weight based upon only the fluorocarbons present, and do not include the weights of any acids present in the calculation unless otherwise indicated. The following Examples employ the NRTL interaction parameters identified above. In the following Examples, each stage is based upon a 100% operational or performance efficiency. The following Examples compare the application of conventional distillation methods with the processes of this invention for various mixtures of PFC-116 with other fluorocarbon impurities. In all examples, the numbering of separation stages is based on the convention that the condenser is counted as stage number 1. For purposes of comparison, a 98% recovery of essentially pure PFC-116 containing 1 ppm or less of impurity has been chosen as a goal.

EXAMPLES

Comparative Example 1

In this Example, conventional distillation is used in a column with 62 stages for purifying a feed stream containing 500 lb/hr of hexafluoroethane (PFC-116) and 0.5 lb/hr of chlorotrifluoromethane (CFC-13) (a nominal concentration of 1000 ppm). The feed stream is introduced onto stage 25. The feed is introduced at a temperature of −25 degrees C., with the column condenser pressure set at 124.7 psia and the column base pressure 3 psi higher. The column distillate/feed ratio is varied to get the specified product recovery, and the reflux ratio is varied to approximately meet the hexafluoroethane specification of 1 ppm of chlorotrifluoromethane in the column bottoms. In this Example the distillate/feed ratio refers to the ratio of the total moles of all species being removed in the distillate to the moles of PFC-116 being fed to the column. The bottoms temperature is −26 degrees C. and the distillate temperature is −27 degrees C. The hexafluoroethane product leaves from the bottom of the column; the chlorotrifluoromethane and some of the hexafluoroethane leave in the column distillate. The results are shown in Table 9 below.

TABLE 9

| Dist./Feed Ratio | Reflux Ratio | ppm CFC-13 in Bottoms | Lb/hr PFC-116 in Bottoms | % PFC-116 Recovery |
|---|---|---|---|---|
| 0.10 | 170 | 1.0 | 451 | 90 |
| 0.05 | 400 | 1.0 | 476 | 95 |
| 0.02 | 1520 | 1.0 | 491 | 98 |

Conventional distillation can recover about 98% of the PFC-116 in the feed while producing a product with about 1 ppm of CFC-13 by using a reflux ratio of over 1000 to 1. Such a reflux ratio would require relatively large equipment and an uneconomically high heating and cooling energy load. The recovery efficiency of the PFC-116 is limited because an azeotropic or azeotrope-like composition is formed between PFC-116 and CFC-13 that exits the column as the distillate in this Example. However, this Example illustrates how the concentration of CFC-13 can be reduced from a first or feed mixture comprising PFC-116 and CFC-13 by using azeotropic distillation.

Comparative Example 2

In this Example, conventional distillation is used in a column with 62 stages for purifying a feed stream containing 500 lb/hr of hexafluoroethane (PFC-116), 0.5 lb/hr of chlorotrifluoroethane (CFC-13) and 0.5 lb/hr of trifluoromethane (HFC-23) (a nominal concentration of 1000 ppm each). The feed stream is introduced onto stage 25. The feed is introduced at a temperature of –25 degrees C., with the column condenser pressure set at 154.7 psia and the column base pressure 3 psi higher. The column distillate/feed ratio is varied to get the specified product recovery, and the reflux ratio is varied to meet the hexafluoroethane specification of 1 ppm of CFC-13 plus HFC-23 in the column bottoms. In this Example the distillate/feed ratio refers to the ratio of the total moles of all species being removed in the distillate to the moles of PFC-116 in the feed to the column. The bottoms temperature is –19 degrees C. and the distillate temperature varies from –21 to –25 degrees C. depending on the distillate/feed ratio and reflux ratio. The hexafluoroethane product leaves from the bottom of the column; the HFC-23, CFC-13 and a portion of the hexafluoroethane leave in the column distillate. The results are shown in Table 10 below.

TABLE 10

| Dist./ Feed Ratio | Reflux Ratio | ppm CFC-13 in Bottoms | ppm HFC-23 in Bottoms | Lb/hr PFC-116 in Bottoms | % PFC-116 Recovery |
| --- | --- | --- | --- | --- | --- |
| 0.10 | 161 | 1.0 | <0.01 | 452 | 90 |
| 0.05 | 377 | 1.0 | <0.01 | 477 | 95 |
| 0.02 | 1526 | 1.0 | <0.01 | 492 | 98 |

Table 10 shows that the ability to obtain substantially pure PFC-116 with this process is the same as in Comparative Example 1 in that the presence of CFC-13 limits the efficiency of the process. Even though the HFC-23 can be removed to relatively low levels by using conventional distillation, when in combination with CFC-13, an uneconomical reflux ratio of about 1500 to 1 is required to achieve an overall impurity level of less than about 1 ppm and 98% recovery of PFC-116. The recovery efficiency of the PFC-116 is limited because azeotropic or azeotrope-like compositions are formed between PFC-116 and CFC-13, and PFC-116 and HFC-23. However, this Example illustrates how the concentration of HFC-23 can be reduced from a feedstock or first mixture comprising PFC-116 and at least HFC-23 by using azeotropic distillation.

Example 1

In this Example, azeotropic distillation with HCl is used in a column with 62 stages for purifying a feed stream coming 500 lb/hr of hexafluoroethane (PFC-116) and 0.5 lb/hr of chlorotrifluoromethane (CFC-13), the same composition as Comparative Example 1. To this is added 250 lb/hr of anhydrous HCl. The feed stream is introduced onto stage 41. The feed is introduced at a temperature of –30 degrees C., with the column condenser pressure set at 264.7 psia and the column base pressure 3 psi higher. The column distillate/ feed ratio is varied to get the specified product recovery, and the reflux ratio is varied to approximately meet the hexafluoroethane specification of 1 ppm of chlorotrifluoromethane in the column distillate. In this Example the distillate/feed ratio refers to the ratio of the total moles of all species being removed in the distillate to the moles of PFC-116 and HCl in the feed to the column. The distillate temperature is –27 degrees C. and the bottom column temperature varies from –26 to –21 degrees C. depending the distillate/feed ratio. In this Example, the hexafluoroethane product leaves in the column distillate stream as an azeotropic or azeotrope-like composition with HCl; the remaining HCl and chlorotrifluoromethane exit in the column bottoms. The results are shown in Table 11 below.

TABLE 11

| Dist./Feed Ratio | Reflux Ratio | ppm CFC-13 Overhead | Lb/hr PFC-116 in Overhead | % PFC-116 Recovery |
| --- | --- | --- | --- | --- |
| 0.83 | 12.5 | 1.1 | 450 | 90 |
| 0.88 | 13.2 | 1.1 | 475 | 95 |
| 0.91 | 14.6 | 1.0 | 490 | 98 |
| 0.92 | 16.4 | 1.0 | 495 | 99 |

The above Example shows that PFC-116 may be recovered with an impurity level of less than about 1 ppm of CFC-13 and a yield of 99% by using HCl as an azeotroping agent.

The PFC-116 and azeotroped HCl are then cooled to a temperature below about –50 degrees C. and the two layers separated in a decanter. The PFC-116 layer is then sent to a second distillation column for removing the remaining HCl as an overhead azeotrope; the recovered HCl may then be recycled to the first distillation column. The PFC-116 from the bottoms of the second distillation column is then given any final purification steps required by using procedures well known to those skilled in the art, e.g., passing the PFC-116 through a resin bed for deacidification.

Example 2

Example 1 is substantially repeated but with the addition of 0.3 lb/hr each of HCFC-22 and HFC-125 to the previous feed mixture of PFC-116 and CFC-13. The results are substantially identical to the previous Example 1 except that the removal of HCFC-22 and of HFC-125 to the bottom stream is even more efficient than that of CFC-13. The overhead product PFC-116 in this case contains only 0.001 ppm each of HCFC-22 and HFC-125 along with the previously reported amount of CFC-13.

Example 3

In this Example, azeotropic distillation with HCl is used in a first column with 62 stages for purifying a feed stream containing 500 lb/hr of hexafluoroethane (PFC-116), 0.5 lb/hr of chlorotrifluoromethane (CFC-13), and 0.5 lb/hr of trifluoromethane (HFC-23), which corresponds to the composition of Comparative Example 2, plus an added 250 lb/hr of anhydrous HCl. The feed stream is introduced onto stage 41 of the first distillation column at a temperature of –37 degrees C. A recycle stream from a second distillation column containing 604 lb/hr PFC-116, <0.01 lb/hr CFC-13, 9.9 lb/hr HFC-23, 487 lb/hr HCl is introduced to the first distillation column without heating or cooling at stage 21. The first column condenser pressure is set at 264.7 psia and the first column base pressure 3 psi higher. The first column is operated at a 10/1 reflux ratio. The column distillate rate is varied so that 99.5% of the total PFC-116 fed to the column is recovered in the column distillate. The distillate temperature is –27 degrees C. and the bottom column temperature is –14 degrees C. The results of this distillation are shown in Table 12.

TABLE 12

(First Column)

| Reflux Ratio | ppm CFC-13 in Overhead | ppm HFC-23 in Overhead | Lb/hr PFC-116 in Overhead | % PFC-116 Recovery |
|---|---|---|---|---|
| 10 | 0.14 | 8927 | 1099 | 99.5 |

The 99.5% PFC-116 recovery is calculated as the percent of total PFC-116 in the column (feed stock plus recycle) which is recovered in the distillate. In the first column the majority of the hexafluoroethane exits in the column distillate stream as an azeotropic or azeotrope-like composition with HCl along with a portion of the HFC-23; the remaining HCl, HFC-23 and the CFC-13 leave in the first column bottoms. On an HFC-23 basis, 0.5 lb/hr of HFC-23 enters the first column as the feed stock and an additional 9.9 lb/hr with the recycle stream. Leaving the column, 0.5 lb/hr of HFC-23 is in the bottoms stream and 9.9 lb/hr of HFC-23 is in the distillate. By increasing the total HFC-23 content in the first column, the relative volatility of HFC-23 is such that all the HFC-23 entering the first column as a feedstock is forced to the bottom of the first column and removed in the bottom stream. The remainder of the HFC-23 exits the first column via the distillate, but is recycled back to this first column by way of the decanter and second column the overall system as detailed below.

The HCl-hexafluoroethane azeotropic or azeotrope-like composition is then cooled to −55 degrees C. and fed to a decanter for phase separation. The results of the decantation step are given below in the Table 13:

TABLE 13

(Decanter)

| Component (Lb/hr) | Stream from First Column Distillate-Feed Stream (Lb/hr) | HCl-Rich Phase From Decanter Top Stream (Lb/hr) | PFC-116 Rich Phase From Decanter Bottom Stream |
|---|---|---|---|
| HCl | 487 | 310 | 177 |
| CFC-13 | <0.01 | <0.01 | <0.01 |
| HFC-23 | 9.9 | 1.0 | 8.9 |
| PFC-116 | 1099 | 110 | 989 |

The HCl-rich phase, which forms in the upper region of the decanter, is returned in a recycle stream to the first column.

The hexafluoroethane-rich phase, which forms in the bottom region of the decanter, is then fed to a second distillation column with 52 theoretical stages with the feed at stage 10. The second column condenser pressure is set at 324.7 psia. The second column is operated at a reflux ratio of 3/1. The distillate temperature is −20 degrees C. and the bottom column temperature is 7.5 degrees C. In this second column, the purified hexafluoroethane leaves the bottom of the column, and the recycle stream to the first column leaves in the overhead. The results of this distillation are shown in Table 14. In this Example, the bottoms/feed ratio is the ratio of the moles of PFC-116 exiting the column in the column bottoms to the moles of PFC-116 being fed to the column.

TABLE 14

(Second Column)

| Bott./Feed Ratio | Reflux Ratio | ppm CFC-13 in Bottoms | ppm HFC-23 in Bottoms | ppm HCl in Bottoms | Lb/hr PFC-116 in Bottoms | % PFC-116 Recovery |
|---|---|---|---|---|---|---|
| 0.5 | 3 | <0.01 | <0.01 | <0.01 | 494 | 50 |

The bottoms stream from this second column is the product PFC-116, which may then be sent on to further purification if desired. The PFC-116 recovery in the second column is 50% because the remaining approximately 50% of the PFC-116 is recycled to the first column. The overall recovery for the system (first column, decanter, second column) is however 99.0%. This Example shows that substantially pure PFC-116 can be obtained at a high rate of recovery by using azeotropic distillation. The product PFC-116 obtained from the bottoms of the second column from this overall system is substantially free of both halocarbons and HCl. This Example show that the invention can produce a PFC-116 product that is greater than 99.999 wt % PFC-116 based on the weight of all components contained within.

Example 4

In this Example, the amounts of CFC-13 and HFC-23 are increased ten times in comparison to Example 3. Other conditions are essentially the same. The results of this Example are listed below in Tables 15, 16 and 17.

TABLE 15

(First Column)

| Reflux Ratio | ppm CFC-13 in Overhead | ppm HFC-23 in Overhead | Lb/hr PFC-116 in Overhead | % PFC-116 Recovery |
|---|---|---|---|---|
| 10 | 0.69 | 30009 | 1099 | 99.5 |

TABLE 16

(Decanter)

| Component | Feed Stream Lb/hr | Top Stream Lb/hr | Bottom Stream Lb/hr |
|---|---|---|---|
| HCl | 486 | 301 | 185 |
| CFC-13 | <0.01 | <0.01 | <0.01 |
| HFC-23 | 34.1 | 3.4 | 30.7 |
| PFC-116 | 1098.8 | 109.9 | 988.9 |

The top stream is recycled back to the first distillation column, and the bottoms stream fed to the second distillation column as in Example 3.

TABLE 17

(Second Column)

| Bott./Feed Ratio | Reflux Ratio | ppm CFC-13 in Bottoms | ppm HFC-23 in Bottoms | ppm HCl in Bottoms | Lb/hr PFC-116 in Bottoms | % PFC-116 Recovery |
|---|---|---|---|---|---|---|
| 0.5 | 3 | <0.01 | <0.01 | <0.01 | 494 | 50 |

The distillate stream from the second column is recycled back to the first column as in Example 3.

This Example demonstrates that PFC-116/HCl azeotropic distillation can be used for purifying a PFC-116 feedstock or product that has ten times the amount of CFC-13 and HFC-23 as Example 3 and Comparative Example 2. The product PFC-116 obtained from the bottoms of the second column from this overall system is substantially free of both halocarbons and HCl. The overall recovery of PFC-116 is 99%. This Example shows that the invention can produce a PFC-116 product that is greater than 99.999 wt % PFC-116 based on the weight of all components contained within.

Example 5

In this Example, azeotropic distillation is used to purify HCl in a column with 52 stages. The feed stream contains 250 lb/hr of anhydrous HCl, 100 lb/hr of hexafluoroethane (PFC-116), 0.5 lb/hr of chlorotrifluoromethane (CFC-13), and 0.5 lb/hr of trifluoromethane (HFC-23). The feed stream is introduced onto stage 10. The feed is introduced at a temperature of −25 degrees C., with the column condenser pressure set at 314.7 psia and the column base pressure 3 psi higher. The reflux ratio is held constant at 3/1 while the column bottoms/feed ratio is varied. The temperature of the bottoms stream is −21 degrees C.; the temperature of the overhead is −6 to −9 degrees C. depending on the bottom/feed ratio. In this column, substantially pure HCl exits the column bottoms stream and the HCl/PFC-116 azeotrope leaves in the overhead stream along with the other impurities (CFC-13 and HFC-23). In a fully integrated system, the feed to this column would be similar in composition to that of the acid-rich phase from the previously described decanter, and the overhead from this distillation column would be recycled back to the decanter or the first distillation column to improve the overall recovery rate of all ingredients. The results are shown in Table 18 below.

TABLE 18

| Bott./ Feed Ratio | ppm CFC-13 in Bottoms | ppm HFC-23 in Bottoms | ppm PFC-116 in Bottoms | Lb/hr HCl in Bottoms | % HCl Recovery |
|---|---|---|---|---|---|
| 0.65 | <0.01 | <0.01 | <0.01 | 163 | 65 |
| 0.70 | <0.01 | <0.01 | <0.01 | 175 | 70 |
| 0.75 | <0.01 | <0.01 | <0.01 | 188 | 75 |
| 0.80 | <0.01 | 0.02 | <0.01 | 200 | 80 |
| 0.85 | 1894 | 1618 | 45354 | 210 | 84 |

Table 18 illustrates that the impurities in the product HCl can be substantially removed by performing a distillation operation under appropriate conditions. The level of impurities remains relatively low as the bottom/feed ratio is increased from 0.65 to 0.80, but at a bottom/feed ratio of about 0.85 there is insufficient HCl in the column to carry off the impurities in the overhead stream, and the impurity level in the HCl sharply increases to an undesirable level. The impurity concentration increases when the amount of HCl in the distillation column is less than that necessary to form the PFC-116/HCl azeotropic or azeotrope-like compositions, e.g., less than about 62 mole percent of HCl. The overall HCl recovery rate that can be achieved by using the processes of this invention in an integrated system, i.e., with recycle of the overhead stream, would be near 100%.

Comparative Example 3

In this Example, azeotropic distillation is used to obtain purified HF from a mixture containing PFC-116 within a distillation column having 62 stages. The feed stream contains 1900 lb/hr of anhydrous HF and 690 lb/hr of hexafluoroethane (PFC-116). The feed stream is introduced onto stage 25. The feed is introduced at a temperature of −25 degrees C., with the column condenser pressure set at 164.7 psia and the column base pressure 3 psi higher. The reflux ratio is held constant at 2/1 while the column distillate/feed ratio is varied. The temperature of the bottoms stream is 104 degrees C.; the temperature of the overhead is −17 to −18 degrees C. depending on the distillate/feed ratio. In this Example the distillate/feed ratio refers to the ratio of the total moles of all species being removed in the distillate to the moles of PFC-116 in the feed to the column. In this column, the substantially pure HF exits in the column bottoms stream and the HF/PFC-116 azeotropic or azeotrope-like composition exits in the overhead stream. The results are shown in Table 19 below.

TABLE 19

| Dist./ Feed Ratio | ppm PFC-116 in Bottoms | Lb/hr HF in Bottoms | Lb/hr PFC-116 in Overhead | Lb/hr HF in Overhead | % HF Recovery |
|---|---|---|---|---|---|
| 2.0 | 0.0 | 1800 | 690 | 100 | 94.7 |
| 1.5 | 0.0 | 1850 | 690 | 50 | 97.4 |
| 1.25 | 0.0 | 1875 | 690 | 25 | 98.7 |
| 1.1 | 0.0 | 1890 | 690 | 10 | 99.5 |

This Example shows that the HF/PFC-116 azeotropic or azeotrope-like compositions have a relatively high volatility in comparison to HF thereby enabling substantially all of the PFC-116 to be removed from the HF as an azeotrope composition. This process forms an overhead stream that consists essentially of PFC-116/HF mixture. In order to recover the PFC-116 as a pure product, the PFC-116 could be scrubbed with water

Comparative Example 4

In this Example, azeotropic distillation is used to purify PFC-116 from a mixture with HF in a column with 62 stages. The feed stream contains 100 lb/hr of anhydrous HF (5 moles) and 13,112 lb/hr of hexafluoroethane (PFC-116) (95 moles). The feed stream is introduced onto stage 25. The feed is introduced at a temperature of −25 degrees C., with the column condenser pressure set at 164.7 psia and the column base pressure 3 psi higher. The reflux ratio is held constant at 10/1 while the column distillate/feed ratio is varied. The temperature of the overhead stream is −17.7 degrees C.; the temperature of the bottoms is −16.4 to −16.9 degrees C. depending on the distillate/feed ratio. In this column, the goal is to take the HF/PFC-116 azeotrope overhead and recover a purified PFC-116 in the bottoms stream. In this Example, the distillate-to-feed ratio refers to the ratio of total moles of all species being removed in the distillate to the moles of HF in the feed to the column. The results are shown in Table 20 below.

TABLE 20

| Dist./ Feed Ratio | ppm HF in Bottoms | Lb/hr PFC-116 in Bottoms | Lb/hr PFC-116 in Overhead | Lb/hr HF Overhead | % PFC-116 Recovery |
|---|---|---|---|---|---|
| 5 | 3683 | 10,094 | 3018 | 63 | 77.0 |
| 4 | 4640 | 10,698 | 2414 | 50 | 81.6 |
| 3 | 5493 | 11,301 | 1811 | 38 | 86.2 |

TABLE 20-continued

| Dist./ Feed Ratio | ppm HF in Bottoms | Lb/hr PFC-116 in Bottoms | Lb/hr PFC-116 in Overhead | Lb/hr HF Overhead | % PFC-116 Recovery |
|---|---|---|---|---|---|
| 2 | 6258 | 11,905 | 1207 | 25 | 90.8 |
| 1 | 6948 | 12,508 | 604 | 13 | 95.4 |

This Example shows a low degree of purification when operating the distillation column under these conditions because the volatility of the HF/PFC-116 azeotrope is similar to PFC-116.

Example 6

In this Example, azeotropic distillation is used to separate PFC-116 from a mixture with HF by adding HCl to the mixture. A column with 62 stages is used with the feed introduced onto stage 25. The feed stream contains 1000 lb/hr of anhydrous HF (50 moles), 6,901 lb/hr of hexafluoroethane (PFC-116) (50 moles), and 3,646 lb/hr of HCl (100 moles). The feed is introduced at a temperature of −25 degrees C., with the column condenser pressure set at 164.7 psia and the column base pressure 3 psi higher. The reflux ratio is held constant at 3/1 while the column distillate/feed ratio is adjusted to recover 99.9% of the PFC-116 overhead. In this Example the distillate/feed ratio refers to the ratio of the total moles of all species being removed in the distillate to the moles of PFC-116 and HCl in the feed to the column. The temperature of the overhead stream is −41.6 degrees C.; the temperature of the bottoms is −20.2 degrees C. In this column, the goal is to take the HCl/PFC-116 azeotropic or azeotrope-like composition overhead and leave the pure HF and remaining HCl in the bottoms stream. The results are shown in Table 21 below.

TABLE 21

| ppm HF in Overhead | Lb/hr HCl in Overhead | Lb/hr PFC-116 in Overhead | Lb/hr PFC-116 in Bottoms | % PFC-116 Recovery |
|---|---|---|---|---|
| 0.0 | 2960 | 6894 | 6.9 | 99.9 |

In contrast to comparative Examples 3 and 4, where HF and PFC-116 were virtually inseparable, this Example shows how the separation of HF and PFC-116 may be effected by forming an HCl/PFC-116 azeotropic or azeotrope-like composition. Best results are obtained when the quantity of HCl is sufficient to form the azeotropic or azeotrope-like composition. The HCl/HF mixture in the bottoms stream can be separated by distillation. If the amount of HCl is minimized, the HF can be recycled to a PFC-116 manufacturing process, i.e., a relatively small amount of HCl will not interfere with the PFC-116 reaction. The HCl/PFC-116 azeotropic or azeotrope-like composition is readily separable into its individual components by the previously described decantation and distillation processes.

Comparative Example 5

In this Example, conventional distillation is used in a column with 62 stages for purifying a feed stream containing 500 lb/hr of hexafluoroethane (PFC-116) and 0.5 lb/hr of difluoromethane (HFC-32) (a nominal concentration of 1000 ppm). The feed stream is introduced onto stage 25. The feed is introduced at a temperature of −5 degrees C., with the column condenser pressure set at 264.7 psia and the column base pressure 3 psi higher. The column distillate/feed ratio is varied to get the specified product recovery, and the reflux ratio is varied to approximately meet the hexafluoroethane specification of 1 ppm of difluoromethane in the column bottoms. In this Example the distillate/feed ratio refers to the ratio of the total moles of all species being removed in the distillate to the moles of PFC-116 in the feed to the column. The bottoms temperature and the distillate temperature vary as shown. The hexafluoroethane product leaves from the bottom of the column; the difluoromethane and some of the hexafluoroethane leave in the column distillate. The results are shown in Table 22 below.

TABLE 22

| Dist./ Feed Ratio | Reflux Ratio | Distillate 116 Lb/hr | Distillate 32 Lb/hr | Distillate Temp Deg C. | Bottoms 116 Lb/hr | Bottoms 32 PPM | Temp Deg C. | % PFC-116 Recovery in Bottoms |
|---|---|---|---|---|---|---|---|---|
| 0.10 | 13.2 | 48.7 | 0.50 | −1.8 | 451 | 1.0 | 0 | 90.3 |
| 0.05 | 28.8 | 23.7 | 0.50 | −2.9 | 476 | 1.0 | 0 | 95.3 |
| 0.02 | 75.6 | 8.7 | 0.50 | −5.2 | 491 | 1.0 | 0 | 98.3 |
| 0.01 | 151 | 3.7 | 0.50 | −6.3 | 496 | 1.0 | 0 | 99.3 |

Conventional distillation can recover about 99% of the PFC-116 in the feed while producing a product with about 1 ppm of HFC-32 by using a reflux ratio of over 150 to 1. However, such a reflux ratio would require relatively large equipment and an uneconomically high heating and cooling energy load. The recovery efficiency of the PFC-116 is limited because an azeotropic or azeotrope-like composition is formed between PFC-116 and HFC-32 that exits the column as the distillate in this Example. However, this Example illustrates how the concentration of HFC-32 can be reduced from a first or feed mixture comprising PFC-116 and HFC-32 by using azeotropic distillation.

Example 7

In this Example, azeotropic distillation is used to separate PFC-116 from a mixture with HFC-32 by adding HCl to the mixture. A column with 42 stages is used with the feed introduced onto stage 28. The feed stream contains 500 lb/hr of hexafluoroethane (PFC-116), 0.5 lb/hr of HFC-32, and 250 lb/hr of HCl. The feed is introduced at a temperature of −30 degrees C., with the column condenser pressure set at 264.7 psia and the column base pressure 3 psi higher. The column distillate/feed ratio is held constant while the reflux ratio is varied. In this Example the distillate/feed ratio refers to the ratio of the total moles of all species being removed in the distillate to the moles of PFC-116 and HCl in the feed to the column. The temperature of the overhead stream is −26.8 degrees C.; the temperature of the bottoms is −12.0 degrees C. In this column, the goal is to take the HCl/PFC-116 azeotropic or azeotrope-like composition overhead and leave the HFC-32 in the bottoms stream. The results are shown in Table 23 below.

TABLE 23

| Dist./ Feed Ratio | Reflux Ratio | Distillate | | | Bottoms | | | % PFC-116 Recovery in Distillate |
|---|---|---|---|---|---|---|---|---|
| | | 116 Lb/hr | HCl Lb/hr | 32 ppm | 116 Lb/hr | HCl pph | 32 Lb/hr | |
| 0.95 | 10 | 500 | 231 | <.01 | <.01 | 19 | 0.5 | 100 |
| 0.95 | 3 | 500 | 231 | <.01 | <.01 | 19 | 0.5 | 100 |
| 0.95 | 1 | 500 | 231 | <.01 | <.01 | 19 | 0.5 | 100 |

In contrast to Comparative Example 5, when HCl is added to the 32/116 mixture, essentially complete separation of the HFC-32 and PFC-116 may be effected. The PFC-116/HCl product exiting as the distillate may be separated by decanting and subsequent azeotropic distillation. The HFC-32/HCl mixture exiting the bottoms may be separated by conventional distillation.

Comparative Example 6

In this Example, conventional distillation is used in a column with 62 stages for purifying a feed stream containing 500 lb/hr of hexafluoroethane (PFC-116) and 0.5 lb/hr of 1,1,1-trifluoroethane (HFC-143a) (a nominal concentration of 1000 ppm). The feed stream is introduced onto stage 25. The feed is introduced at a temperature of −15 degrees C., with the column condenser pressure set at 64.7 psia and the column base pressure 3 psi higher. The reflux ratio is fixed and the column distillate/feed ratio is varied to get the specified product recovery, with the goal to obtain a maximum of 100 ppm of trifluoroethane in the PFC-116 product. In this Example the distillate/feed ratio refers to the ratio of the total moles of all species being removed in the distillate to the moles of PFC-116 in the feed to the column. The bottoms temperature and the distillate temperature are as shown. The hexafluoroethane product leaves from the top of the column; the trifluoroethane and some of the hexafluoroethane leave in the column bottoms. The results are shown in Table 24 below.

TABLE 24

| Dist./ Feed Ratio | Reflux Ratio | Distillate | | | Bottoms | | | % PFC-116 Recovery Distillate |
|---|---|---|---|---|---|---|---|---|
| | | 116 Lb/hr | 143a ppm | Temp Deg C. | 116 Lb/hr | 143a Lb/hr | Temp Deg C. | Dis-tillate |
| 0.98 | 100 | 490 | 551 | −45.5 | 10 | 0.23 | −44.2 | 98.0 |
| 0.90 | 100 | 450 | 346 | −45.5 | 50 | 0.34 | −44.3 | 90.0 |
| 0.50 | 100 | 250 | 187 | −45.5 | 250 | 0.45 | −44.3 | 50.0 |
| 0.10 | 100 | 50 | 264 | −45.5 | 450 | 0.49 | −44.3 | 10.0 |
| 0.02 | 100 | 10 | 336 | −45.5 | 490 | 0.50 | −44.3 | 2.0 |

At these column pressures and temperatures, conventional distillation cannot produce the desired 100 ppm HFC-143a in the product PFC-116 at a reflux ratio of 100:1 because of the vapor-liquid equilibrium tangent pinch which exists between PFC-116 and HFC-143a. Moreover, column operation to obtain the separation requires extremely cold temperatures and high reflux ratios, the combination of which are extremely expensive to provide.

EXAMPLE 8

In this Example, azeotropic distillation is used to separate PFC-116 from a mixture with HFC-143a by adding HCl to the mixture. A column with 42 stages is used with the feed introduced onto stage 28. The feed stream contains 500 lb/hr of hexafluoroethane (PFC-116), 0.5 lb/hr of HFC-143a, and 250 lb/hr of HCl. The feed is introduced at a temperature of −30 degrees C., with the column condenser pressure set at 264.7 psia and the column base pressure 3 psi higher. The column distillate/feed ratio is held constant while the reflux ratio is varied. In this Example the distillate/feed ratio refers to the ratio of the total moles of all species being removed in the distillate to the moles of PFC-116 and HCl in the feed to the column. The temperature of the overhead stream is −26.8 degrees C.; the temperature of the bottoms is −12.2 degrees C. In this column, the goal is to take the HCl/PFC-116 azeotropic or azeotrope-like composition overhead and leave the HFC-143a in the bottoms stream. The results are shown in Table 25 below.

TABLE 25

| Dist./ Feed Ratio | Reflux Ratio | Distillate | | | Bottoms | | | % PFC-116 Recovery in Distillate |
|---|---|---|---|---|---|---|---|---|
| | | 116 Lb/hr | HCl Lb/hr | 143a ppm | 116 Lb/hr | HCl pph | 143a Lb/hr | |
| 0.95 | 10 | 500 | 231 | <.01 | <.01 | 19 | 0.5 | 100 |
| 0.95 | 3 | 500 | 231 | <.01 | <.01 | 19 | 0.5 | 100 |
| 0.95 | 1 | 500 | 231 | 3.8 | <.01 | 19 | 0.5 | 100 |

In contrast to Comparative Example 6, when HCl is added to the 143a/116 mixture, essentially complete separation of the HFC-143a and PFC-116 may be effected, and in contrast to Comparative Example 6, this is accomplished with both higher temperature and lower reflux ratio operation. The PFC-116/HCl product exiting as the distillate may be separated by decanting and subsequent azeotropic distillation. The HFC-143a/HCl mixture exiting the bottoms may be separated by conventional distillation.

Comparative Example 7

In this Example, conventional distillation is used in a column with 62 stages for purifying a feed stream containing 500 lb/hr of hexafluoroethane (PFC-116) and 0.5 lb/hr of 1,1-difluoroethane (HFC-152a) (a nominal concentration of 1000 ppm). The feed stream is introduced onto stage 25. The feed is introduced at a temperature of −15 degrees C., with the column condenser pressure set at 64.7 psia and the column base pressure 3 psi higher. The reflux ratio is fixed and the column distillate/feed ratio is varied to get the specified product recovery, with the goal to obtain a maximum of 100 ppm of HFC-152a in the PFC-116 product. In this Example the distillate/feed ratio refers to the ratio of the total moles of all species being removed in the distillate to the moles of PFC-116 in the feed to the column. The bottoms temperature and the distillate temperature are as shown. The hexafluoroethane product leaves from the top of the column; the trifluoroethane and some of the hexafluoroethane leave in the column bottoms. The results are shown in Table 26 below.

TABLE 26

| Dist./ Feed Ratio | Reflux Ratio | Distillate | | | Bottoms | | | % PFC-116 Recovery Distillate |
|---|---|---|---|---|---|---|---|---|
| | | 116 Lb/hr | 152a ppm | Temp Deg C. | 116 Lb/hr | 152a Lb/hr | Temp Deg C. | |
| 0.98 | 100 | 489 | 1013 | −45.5 | 11 | 0.01 | −44.3 | 97.8 |
| 0.90 | 100 | 449 | 1065 | −45.5 | 51 | 0.02 | −44.3 | 89.8 |
| 0.50 | 100 | 249 | 1318 | −45.5 | 251 | 0.17 | −44.3 | 49.9 |
| 0.10 | 100 | 50 | 1339 | −45.5 | 475 | 0.43 | −44.3 | 10.0 |
| 0.02 | 100 | 10 | 1271 | −45.5 | 490 | 0.49 | −44.3 | 2.0 |

At these column pressures and temperatures, conventional distillation cannot produce the desired 100 ppm HFC-152a in the product PFC-116 at a reflux ratio of 100:1 because of the vapor-liquid equilibrium tangent pinch which exists between PFC-116 and HFC-152a. Moreover, column operation to obtain the separation requires extremely cold temperatures and high reflux ratios, the combination of which are extremely expensive to provide.

EXAMPLE 9

In this Example, azeotropic distillation is used to separate PFC-116 from a mixture with HFC-152a by adding HCl to the mixture. A column with 42 stages is used with the feed introduced onto stage 28. The feed stream contains 500 lb/hr of hexafluoroethane (PFC-116), 0.5 lb/hr of HFC-152a, and 250 lb/hr of HCl. The feed is introduced at a temperature of −30 degrees C., with the column condenser pressure set at 264.7 psia and the column base pressure 3 psi higher. The column distillate/feed ratio is held constant while the reflux ratio is varied. In this Example the distillate/feed ratio refers to the ratio of the total moles of all species being removed in the distillate to the moles of PFC-116 and HCl in the feed to the column. The temperature of the overhead stream is −26.8 degrees C.; the temperature of the bottom is −11.9 degrees C. In this column, the goal is to take the HCl/PFC-116 azeotropic or azeotrope-like composition overhead and leave the HFC-152a in the bottoms stream. The results are shown in Table 27 below.

TABLE 27

| Dist./ Feed Ratio | Reflux Ratio | Distillate | | | Bottoms | | | % PFC-116 Recovery Distillate |
|---|---|---|---|---|---|---|---|---|
| | | 116 Lb/hr | HCl Lb/hr | 152a ppm | 116 Lb/hr | HCl pph | 152a Lb/hr | |
| 0.95 | 10 | 500 | 231 | <.01 | <.01 | 19 | 0.5 | 100 |
| 0.95 | 3 | 500 | 231 | <.01 | <.01 | 19 | 0.5 | 100 |
| 0.95 | 1 | 500 | 231 | <.01 | <.01 | 19 | 0.5 | 100 |

In contrast to Comparative Example 7, when HCl is added to the 152a/116 mixture, essentially complete separation of the HFC-152a and PFC-116 may be effected without expensive low temperature and high reflux operation. The PFC-116/HCl product exiting as the distillate may be separated by decanting and subsequent azeotropic distillation. The HFC-152a/HCl mixture exiting the bottoms may be separated by conventional distillation.

EXAMPLE 10

This Example demonstrates the existence of azeotropic or azeotrope-like compositions between the binary pair mixtures consisting essentially of HCl and PFC-116; HCl and CFC-13; HCl and HFC-23; HCl and CFC-115; HF and PFC-116; PFC-116 and CFC-13; PFC-116 and HFC-23; PFC-116 and HFC-32; HF and CFC-115; HF and CFC-114; HF and CFC-114a; HF and CFC-113; HF andCFC-113a; HF and HFC-125; CFC-13 and HF; HF and HCFC-22; HF and HFC-143a. To determine the relative volatility of each binary pair, the so-called PTx Method was used. In this procedure, for each binary pair, the total absolute pressure in a PTx cell of known volume was measured at a constant temperature for various known binary compositions. These measurements were then reduced to equilibrium vapor and liquid compositions using the NRTL equation. Samples of selected vapor and liquid sets were obtained and analyzed to verify their respective compositions.

The vapor pressure measured versus the composition in the PTx cell for the HCl and PFC-116; HCl and CFC-13; HCl and HFC-23; HCl and CFC-115; HF and PFC-116; PFC-116 and CFC-13; PFC-116 and HFC-23; PFC-116 and HFC-32; HF and CFC-115; HF and CFC-114; HF and CFC-114a; HF and CFC-113; HF and CFC-113a; HF and HFC-125; CFC-13 and HF; HF and HCFC-22; HF and HFC-143a systems are shown in FIGS. 2 through 20, respectively. The experimental data points are shown in each Figure as solid points on each Figure and the curve is drawn from data calculated using the NRTL equation.

Referring now to FIG. 2. FIG. 2 illustrates graphically the formation of an azeotropic and azeotrope-like composition consisting essentially of HCl and PFC-116 at −20.56 deg C., as indicated by a mixture of about 63.0 mole % HCl and 37.0 mole % PFC-116 having the highest pressure over the range of compositions at this temperature. Based upon these findings, it has been calculated that an azeotropic or azeotrope-like compositions of about 60.5 mole % HCl and 39.5 mole % PFC-116 is formed at −60 deg C. and 80.6 psia and an azeotropic or azeotrope-like composition of about 64.1 mole % HCl and 35.9 mole % PFC-116 is formed at 10 deg C. and 681 psia. Accordingly, the present invention provides an azeotropic or azeotrope-like composition consisting essentially of from about 60.5 to about 64.1 mole % HCl and from about 39.5 to about 35.9 mole % PFC-116, said composition having a boiling point of from about −60 deg C. at 80.6 psia to about 10 deg C. at 681 psia.

Figure 3:
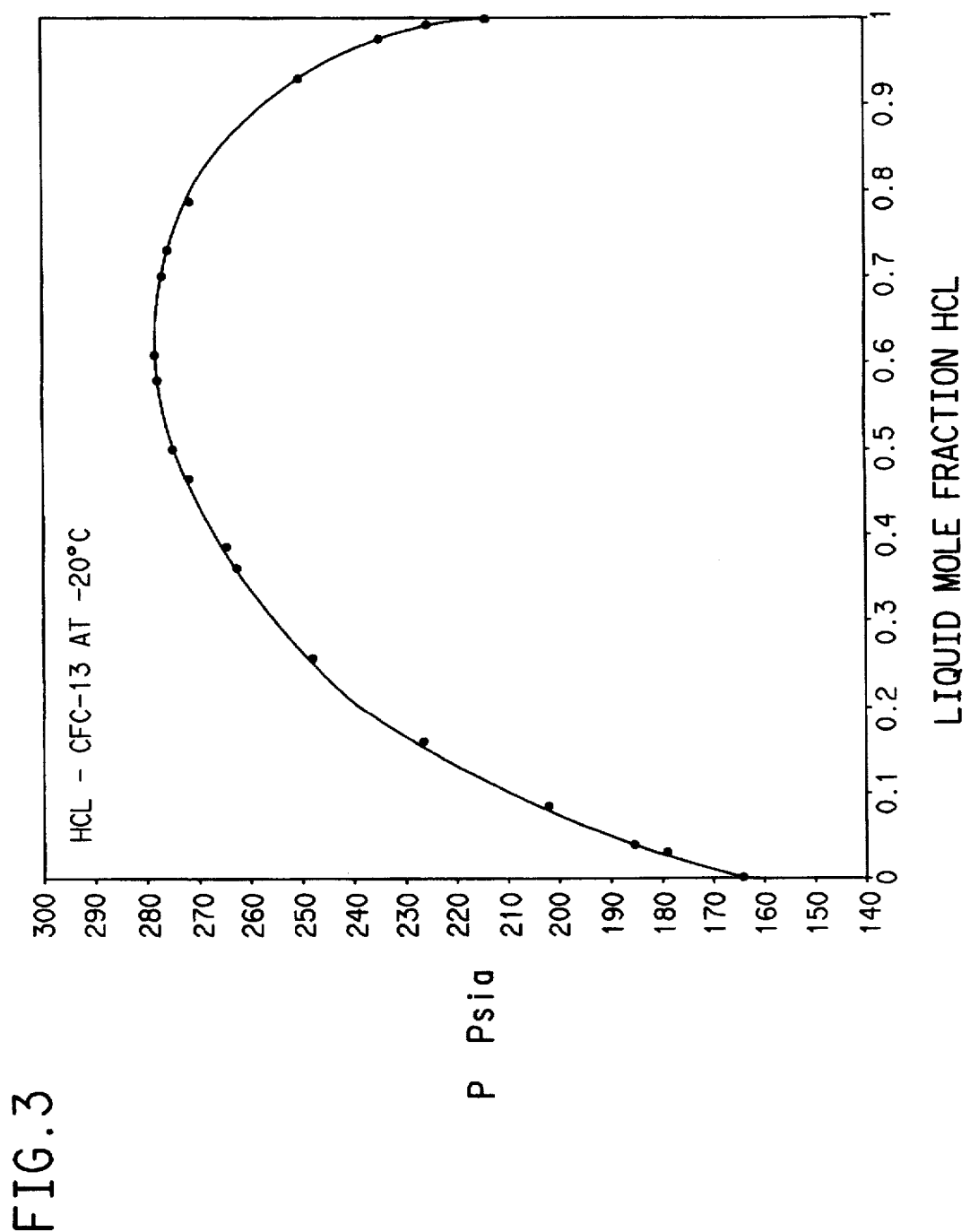
FIG. 3—FIG. 3 is a graphical representation of azeotropic and azeotrope-like compositions consisting essentially of HCl and CFC-13 at a temperature of about −20 deg C.

Referring now to FIG. 3. FIG. 3 illustrates graphically the formation of an azeotropic and azeotrope-like composition consisting essentially of HCl and CFC-13 at −20 deg C., as indicated by a mixture of about 62.4 mole % HCl and 37.6 mole % CFC-13 having the highest pressure over the range of compositions at this temperature. Based upon these findings, it has been calculated that an azeotropic or azeotrope-like compositions of about 62.0 mole % HCl and 38.0 mole % CFC-13 is formed at −50 deg C. and 101 psia and an azeotropic or azeotrope-like composition of about 61.9 mole % HCl and 38.1 mole % CFC-13 is formed at 25 deg C. and 866 psia. Accordingly, the present invention provides an azeotropic or azeotrope-like composition consisting essentially of from about 61.9 to about 62.4 mole % HCl and from about 38.1 to about 37.6 mole % CFC-13, said composition having a boiling point of from about −50 deg C. at 101 psia to about 25 deg C. at 866 psia.

Referring now to FIG. 4. FIG. 4 illustrates graphically the formation of an azeotropic and azeotrope-like composition consisting essentially of HCl and HFC-23 at −20 deg C., as indicated by a mixture of about 56.9 mole % HCl and 43.1 mole % HFC-23 having the highest pressure over the range of compositions at this temperature. Based upon these findings, it has been calculated that an azeotropic or azeotrope-like compositions of about 59.2 mole % HCl and 40.8 mole % HFC-23 is formed at –50 deg C. and 92.7 psia and an azeotropic or azeotrope-like composition of about 49.2 mole % HCl and 50.8 mole % HFC-23 is formed at 25 deg C. and 866 psia. Accordingly, the present invention provides an azeotropic or azeotrope-like composition consisting essentially of from about 59.2 to about 49.2 mole % HCl and from about 40.8 to about 50.8 mole % HFC-23, said composition having a boiling point from about –50 deg C. at 93 psia to about 25 deg C. at 897 psia.

Figure 5:
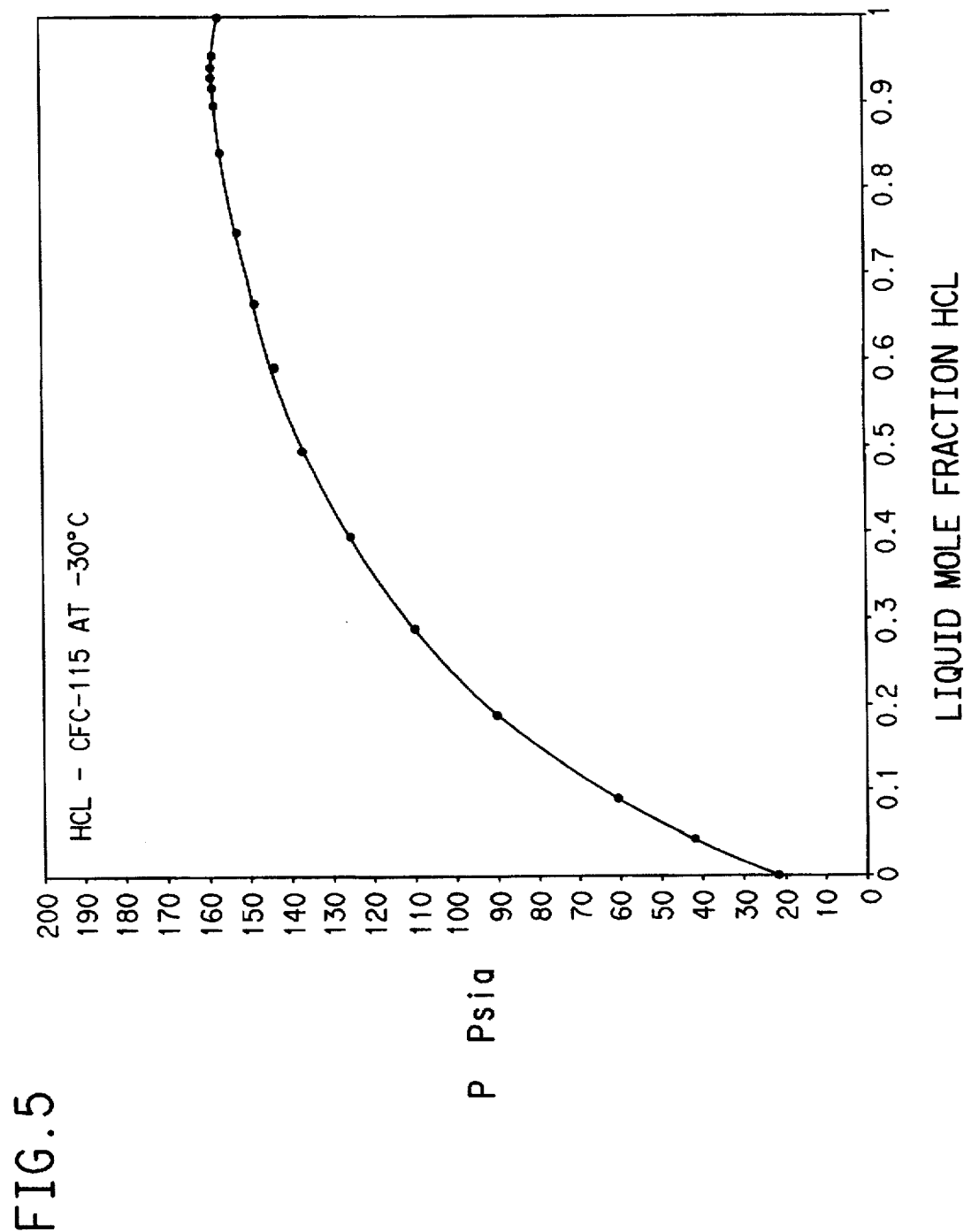
FIG. 5—FIG. 5 is a graphical representation of azeotropic and azeotrope-like compositions consisting essentially of HCl and CFC-115 at a temperature of about −30 deg C.

Referring now to FIG. 5, FIG. 5 illustrates graphically the formation of an azeotropic and azeotrope-like composition consisting essentially of HCl and CFC-115 at –30 deg C., as indicated by a mixture of about 96.3 mole % HCl and CFC-115 having the highest pressure over the range of compositions at this temperature. Based upon these findings, it has been calculated that an azeotropic or azeotrope-like compositions of about 95.0 mole % HCl and 5.0 mole % CFC-115 is formed at –50 deg C. and 75 psia and an azeotropic or azeotrope-like composition of about 99.9 mole % HCl and 0.1 mole % CFC-115 is formed at 25 deg C. and 690 psia. Accordingly, the present invention provides an azeotropic or azeotrope-like composition consisting essentially of from about 95 to about 99.9 mole % HCl and from about 5 to about 0.1 mole % CFC-115, said composition having a boiling point of from about –50 deg C. at 75 psia to about 25 deg C. at 690 psia.

Figure 6:
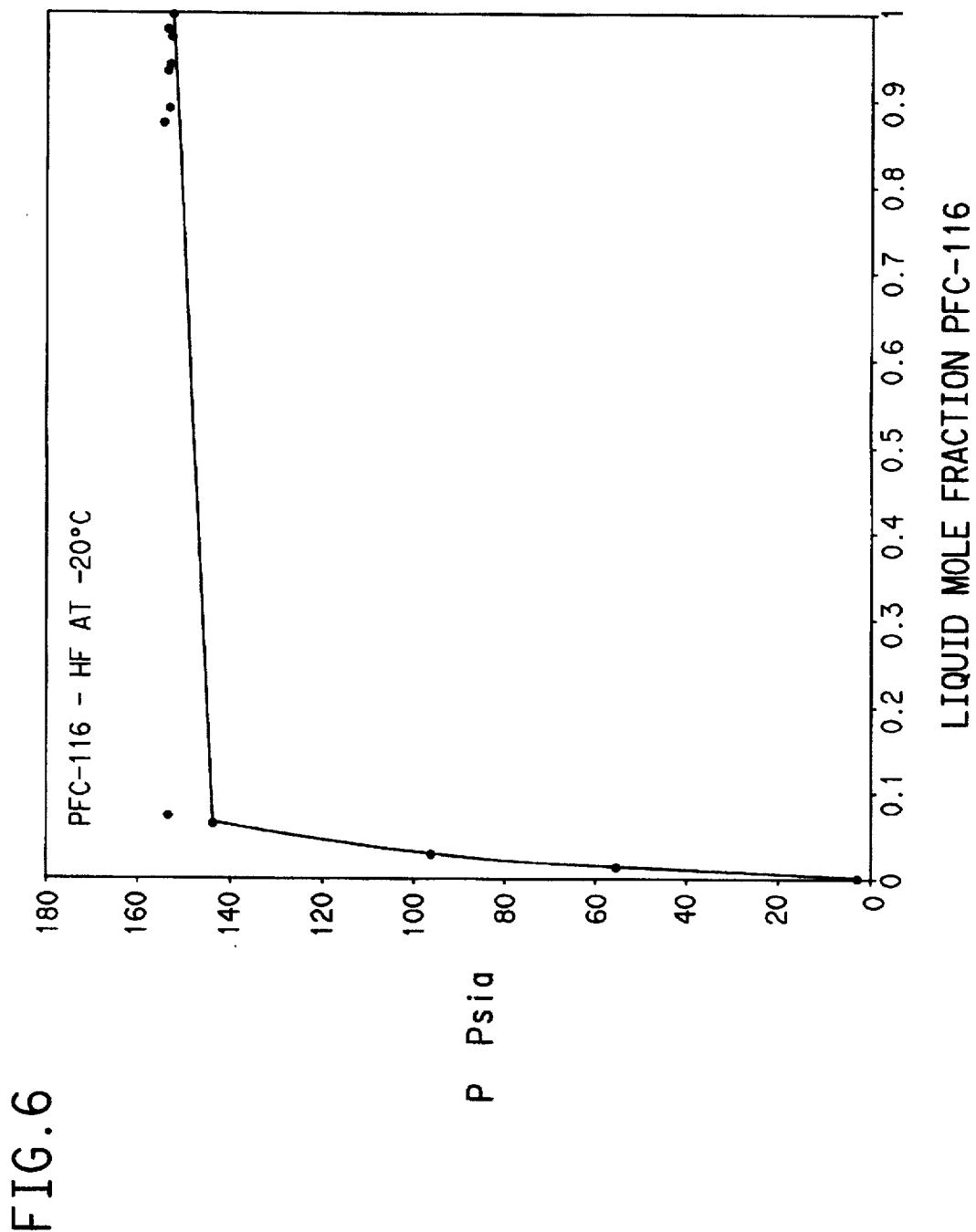
FIG. 6—FIG. 6 is a graphical representation of azeotropic and azeotrope-like compositions consisting essentially of PFC-116 and HF at a temperature of about −20 deg C.

Referring now to FIG. 6, FIG. 6 illustrates graphically the formation of an azeotropic and azeotrope-like composition consisting essentially of HF and PFC-116 at –20 deg C., as indicated by mixtures of HF and PFC-116 having a higher vapor pressure than either pure component at this temperature, with the composition of the vapor space in the maximum pressure region being that of the azeotrope. Sampling of the vapor space and NRTL calculations show that the azeotropic or azeotrope-like composition was about 6.8 mole % HF and 93.2 mole % PFC-116 at this temperature. Based upon these findings, it has been calculated that an azeotropic or azeotrope-like compositions of about 4.2 mole % HF and 95.8 mole % PFC-116 is formed at –50 deg C. and 54.1 psia and an azeotropic or azeotrope-like composition of about 15.1 mole % HF and 84.9 mole % PFC-116 is formed at 8 deg C. and 343 psia. Accordingly, the present invention provides an azeotropic or azeotrope-like composition consisting essentially of from about 4.2 to about 15.1 mole % HF and from about 95.8 to about 84.9 mole % PFC-116, said composition having a boiling point of from about –50 deg C. at 54 psia to about 8 deg C. at 343 psia.

Figure 7:
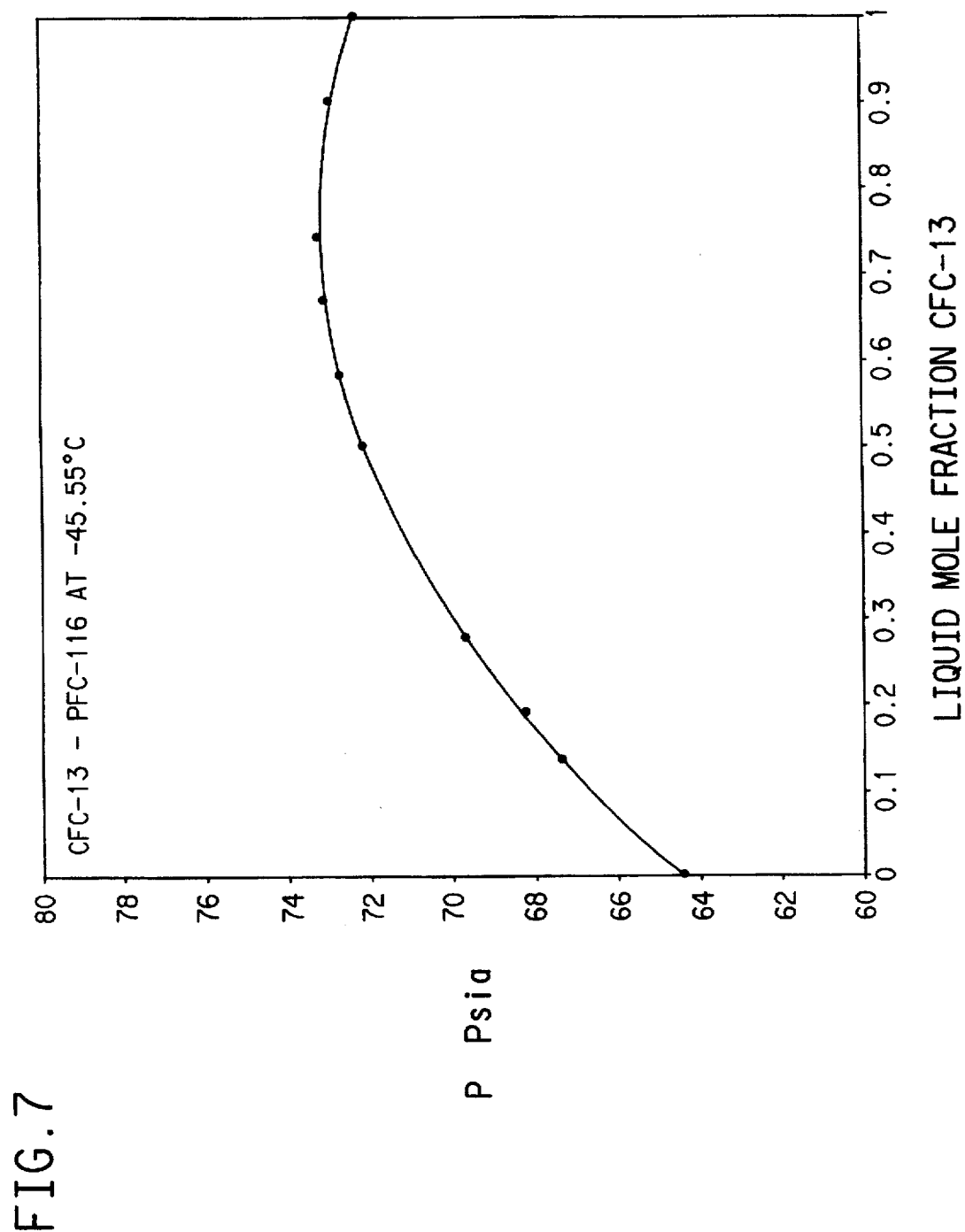
FIG. 7—FIG. 7 is a graphical representation of azeotropic and azeotrope-like compositions consisting essentially of CFC-13 and PFC-116 at a temperature of about −45.55 deg C.

Referring now to FIG. 7, FIG. 7 illustrates graphically the formation of an azeotropic and azeotrope-like composition consisting essentially of CFC-13 and PFC-116 at –45.55 deg C., as indicated by a mixture of about 23.2 mole % PFC-116 and 76.8 mole % CFC-13 having the highest pressure over the range of compositions at this temperature. Based upon these findings, it has been calculated that an azeotropic or azeotrope-like compositions of about 81.2 mole % CFC-13 and 18.8 mole % PFC-116 is formed at –60 deg C. and 41.3 psia and an azeotropic or azeotrope-like composition of about 53.4 mole % CFC-13 and 46.6 mole % PFC-116 is formed at 19 deg C. and 464 psia. Accordingly, the present invention provides an azeotropic or azeotrope-like composition consisting essentially of from about 18.8 to about 46.6 mole % PFC-116 and from about 81.2 to about 53.4 mole % CFC-13 and, said composition having a boiling point of from about –60 deg C. at 41.3 psia to about 19 deg C. at 464 psia.

Figure 8:
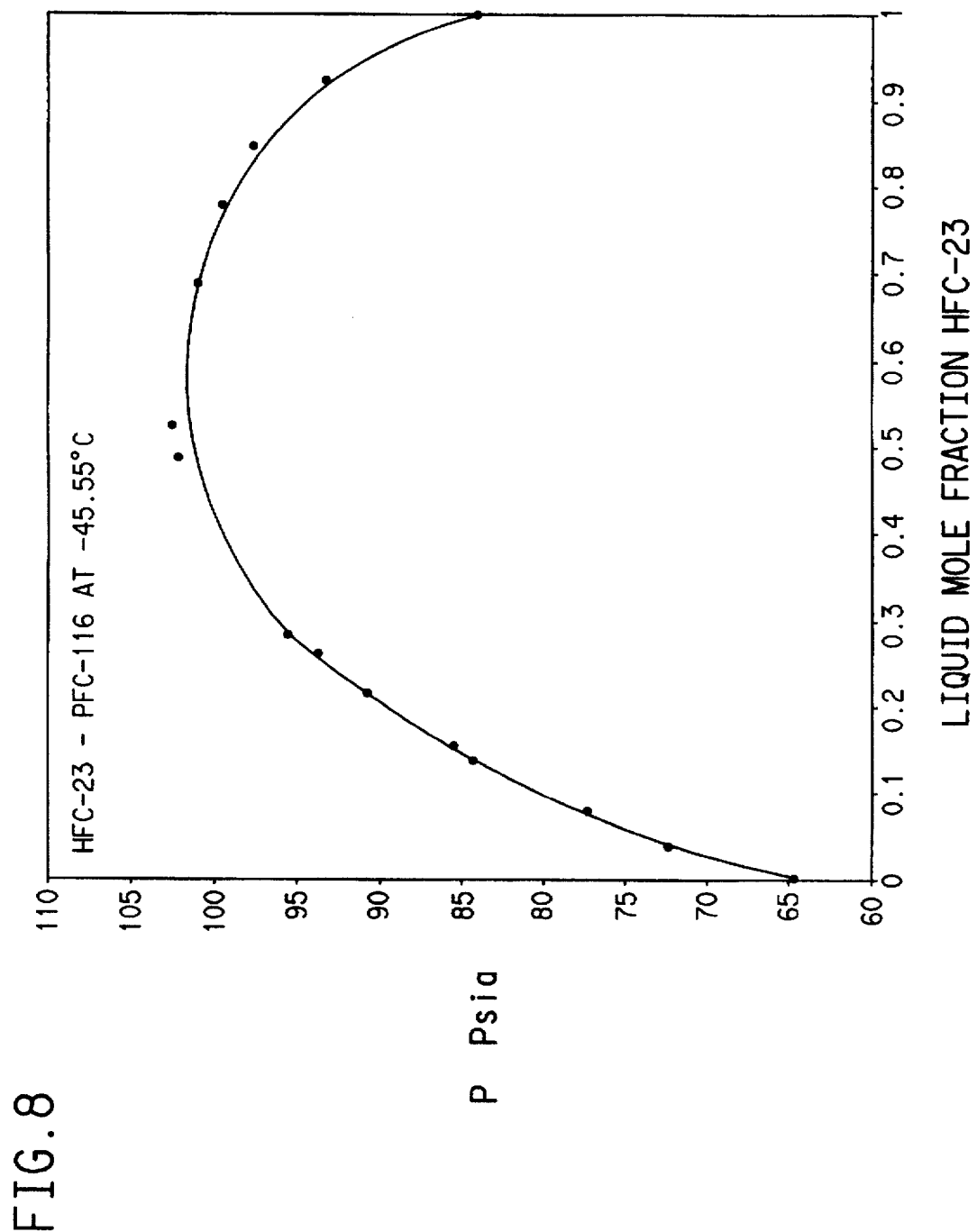
FIG. 8—FIG. 8 is a graphical representation of azeotropic and azeotrope-like compositions consisting essentially of HFC-23 and PFC-116 at a temperature of about −45.55 deg C.

Referring now to FIG. 8, FIG. 8 illustrates graphically the formation of an azeotropic and azeotrope-like composition consisting essentially of HFC-23 and PFC-116 at –45.55 deg C., as indicated by a mixture of about 60.2 mole % HFC-23 and 39.8 mole % PFC-116 having the highest pressure over the range of compositions at this temperature. Based upon these findings, it has been calculated that an azeotropic or azeotrope-like compositions of about 59.5 mole % HFC-23 and 40.5 mole % PFC-116 is formed at –60 deg C. and 58 psia and an azeotropic or azeotrope-like composition of about 65.8 mole % HFC-23 and 34.2 mole % PFC-116 is formed at 10 deg C. and 503 psia. Accordingly, the present invention provides an azeotropic or azeotrope-like composition Consisting essentially of from about 59.5 to about 65.8 mole % HFC-23 and from about 40.5 to about 34.2 mole % PFC-116, said composition having a boiling point of from about –60 deg C. at 58 psia to about 10 deg C. at 503 psia.

Figure 9:
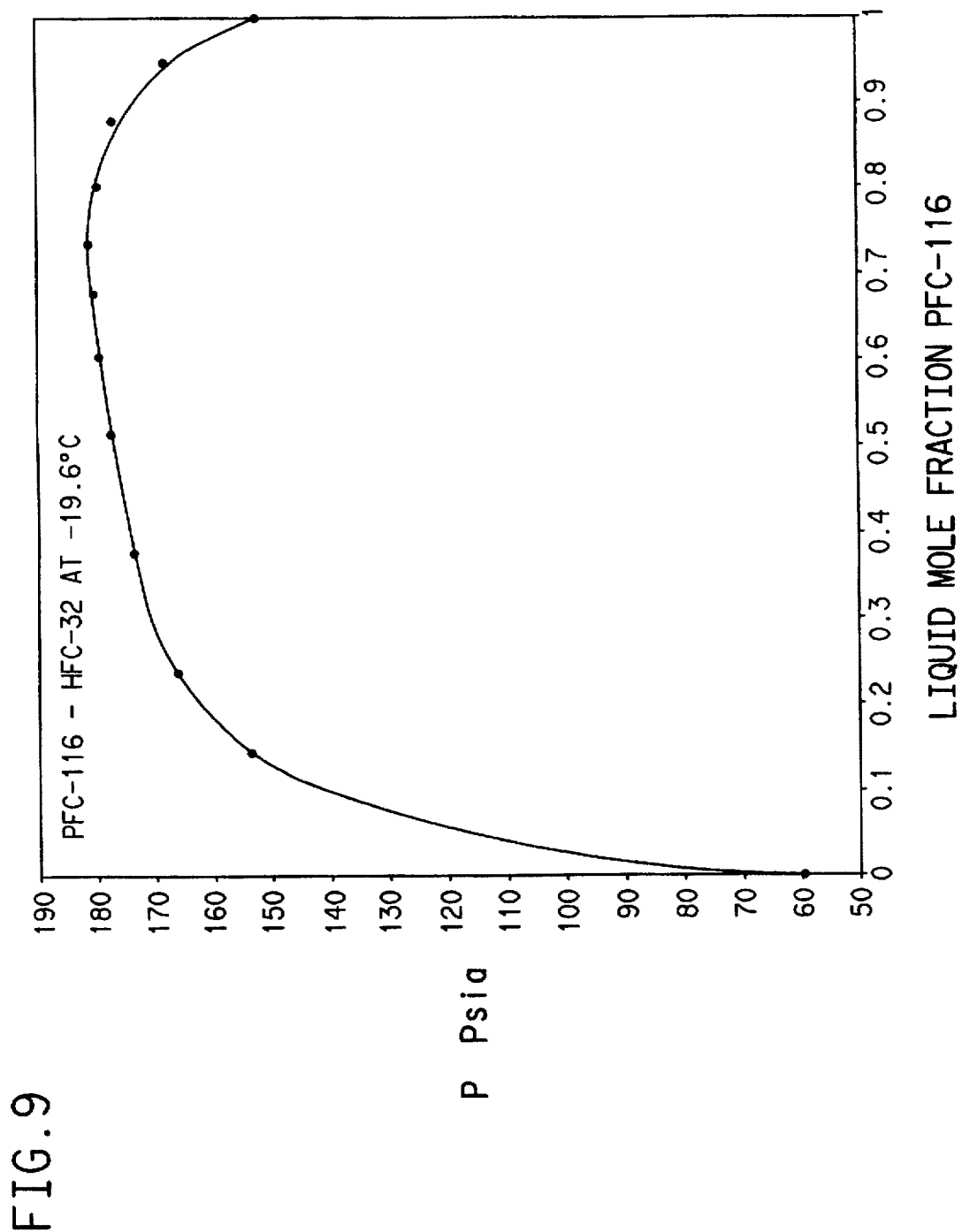
FIG. 9—FIG. 9 is a graphical representation of azeotropic and azeotrope-like compositions consisting essentially of PFC-116 and HFC-32 at a temperature of about −19.6 deg C.

Referring now to FIG. 9, FIG. 9 illustrates graphically the formation of an azeotropic and azeotrope-like composition consisting essentially of HFC-32 and PFC-116 at –19.6 deg C., as indicated by a mixture of about 26.8 mole % HFC-32 and 73.2 mole % PFC-116 having the highest pressure over the range of compositions at this temperature. Based upon these findings, it has been calculated that an azeotropic or azeotrope-like compositions of about 18.3 mole % HFC-32 and 81.7 mole % PFC-116 is formed at –80 deg C. and 14.6 psia and an azeotropic or azeotrope-like composition of about 27.3 mole % HFC-32 and 72.7 mole % PFC-116 is formed at 10 deg C. and 412 psia. Accordingly, the present invention provides an azeotropic or azeotrope-like composition consisting essentially of from about 18.3 to about 26.8 mole % HFC-32 and from about 81.7 to about 73.2 mole % PFC-116, said composition having a boiling point of from about –80 deg C. at 14.6 psia to about 10 deg C. at 412 psia.

Figure 10:
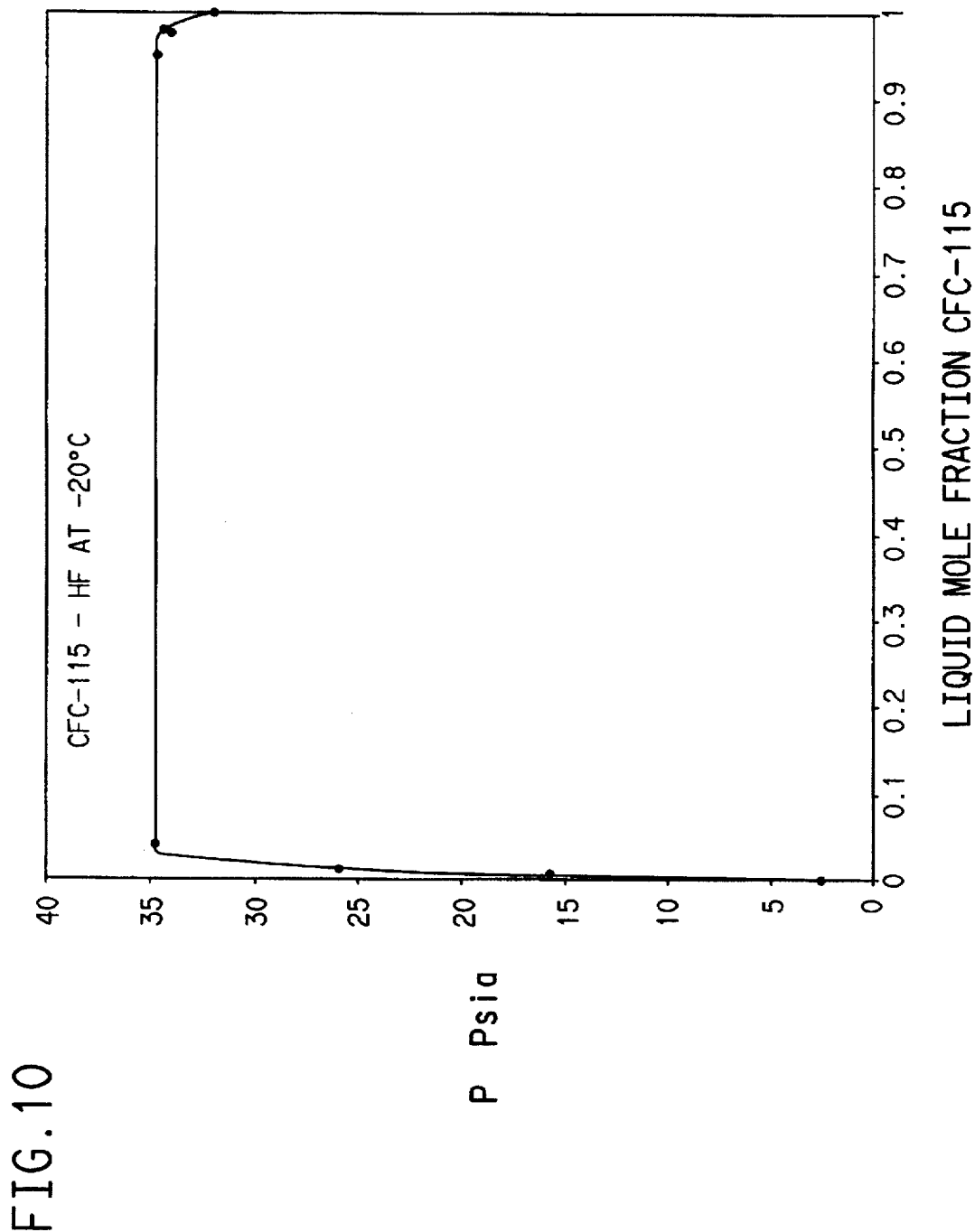
FIG. 10—FIG. 10 is a graphical representation of an azeotropic and azeotrope-like compositions consisting essentially of CFC-115 and HF at a temperature of about −20 deg C.

Referring now to FIG. 10, FIG. 10 illustrates graphically the formation of an azeotropic and azeotrope-like composition consisting essentially of HF and CFC-115 at –20 deg C., as indicated by mixtures of HF and CFC-115 having a higher vapor pressure than either pure component at this temperature, with the composition of the vapor space in the maximum pressure region being that of the azeotrope. Sampling of the vapor space and NRTL calculations showed that the azeotropic or azeotrope-like composition was about 25 mole % HF and 75 mole % CFC-115 at this temperature. Based upon these findings, it has been calculated that an azeotropic or azeotrope-like compositions of about 17 mole % HF and 83 mole % CFC-115 is formed at –60 deg C. and 5.5 psia and an azeotropic or azeotrope-like composition of about 24 mole % HF and 76 mole % CFC-115 is formed at 50 deg C. and 287 psia. Accordingly, the present invention provides an azeotropic or azeotrope-like composition consisting essentially of from about 17 to about 24 mole % HF and from about 83 to about 76 mole % CFC-115, said composition having a boiling point of from about –60 deg C. at 5.5 psia to about 50 deg C. at 287 psia.

Figure 11:
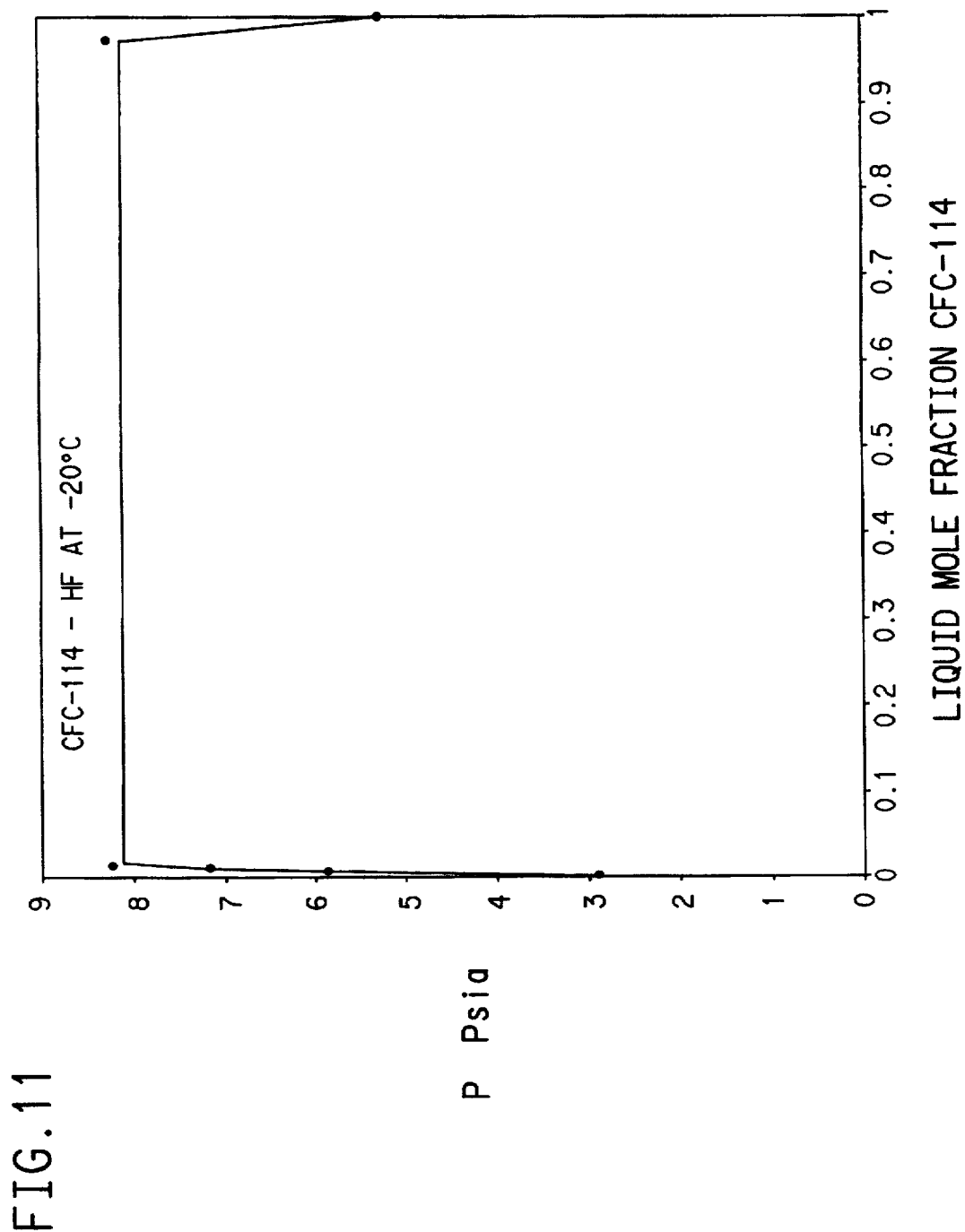
FIG. 11—FIG. 11 is a graphical representation of an azeotropic and azeotrope-like compositions consisting essentially of CFC-114 and HF at a temperature of about −20 deg C.

Referring now to FIG. 11, FIG. 11 illustrates graphically the formation of an azeotropic and azeotrope-like composition consisting essentially of HF and CFC-114 at –20 deg C., as indicated by mixtures of HF and CFC-114 having a higher vapor pressure than either pure component at this temperature, with the composition of the vapor space in the maximum pressure region being that of the azeotrope at a specific temperature and pressure. Sampling of the vapor space and NRTL calculations showed that the azeotropic or azeotrope-like composition was about 67 mole % HF and 33 mole % CFC-114 at this temperature. Based upon these findings, it has been calculated that an azeotropic or azeotrope-like compositions of about 68 mole % HF and 32 mole % CFC-114 is formed at −50 deg C. and 1.6 psia and an azeotropic or azeotrope-like composition of about 50 mole % HF and 50 mole % CFC-114 is formed at 100 deg C. and 427 psia. Accordingly, the present invention provides an azeotropic or azeotrope-like composition consisting essentially of from about 68 to about 50 mole % HF and from about 32 to about 50 mole % CFC-114, said composition having a boiling point of from about −50 deg C. at 1.6 psia to about 100 deg C. at 427 psia.

Figure 12:
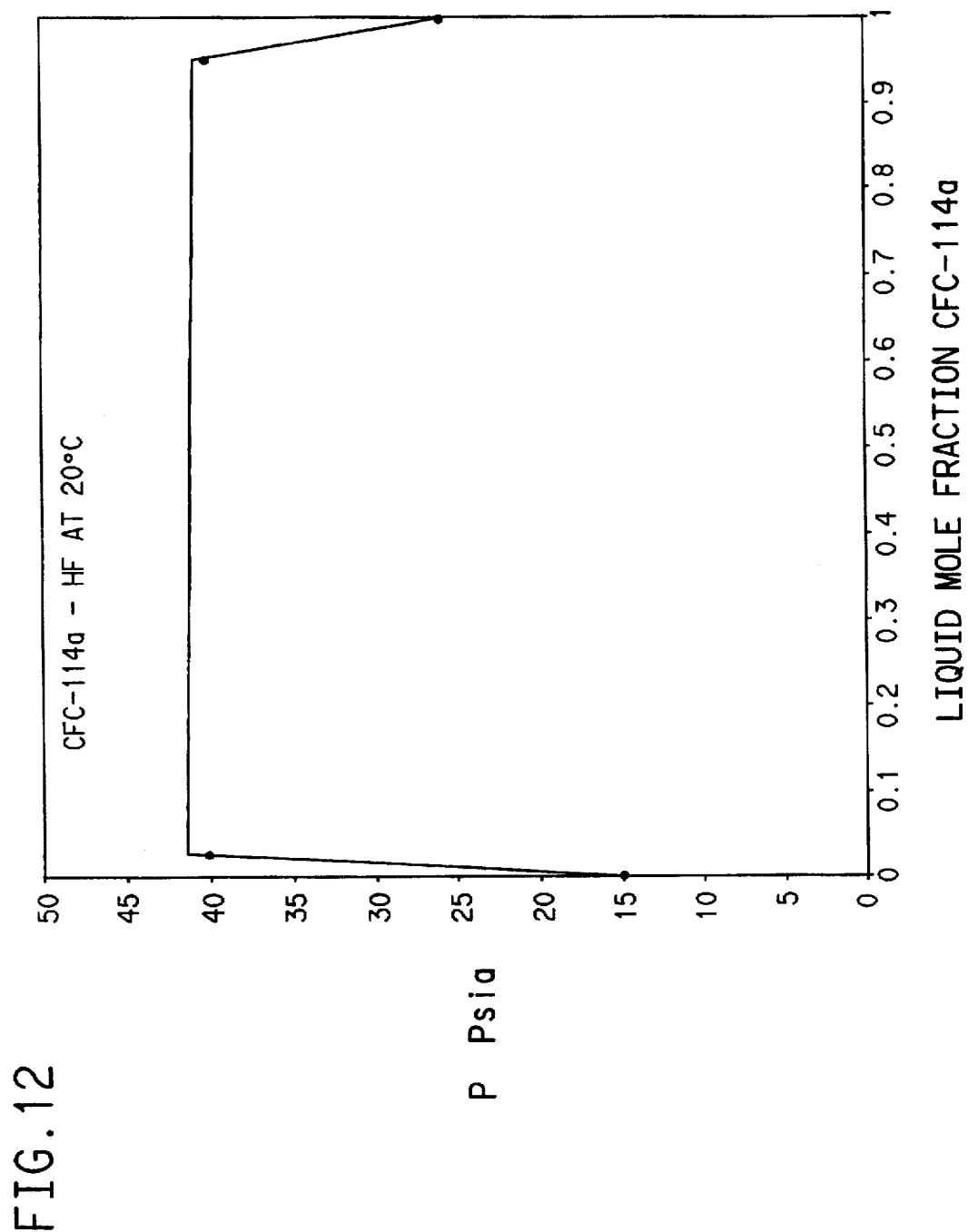
FIG. 12—FIG. 12 is a graphical representation of an azeotropic and azeotrope-like compositions consisting essentially of CFC-114a and HF at a temperature of about 20 deg C.

Referring now to FIG. 12. FIG. 12 illustrates graphically the formation of an azeotropic and azeotrope-like composition consisting essentially of HF and CFC-114a at 20 deg C., as indicated by mixtures of HF and CFC-114a having a higher vapor pressure than either pure component at this temperature, with the composition of the vapor space in the maximum pressure region being that of the azeotrope. Sampling of the vapor space and NRTL calculations showed that the azeotropic or azeotrope-like composition was about 63 mole % HF and 37 mole % CFC-114a at this temperature. Based upon these findings, it has been calculated that an azeotropic or azeotrope-like compositions of about 65 mole % HF and 35 mole % CFC-114a is formed at −25 deg C. and 6.8 psia and an azeotropic or azeotrope-like composition of about 57 mole % HF and 43 mole % CFC-114a is formed at 100 deg C. and 365 psia. Accordingly, the present invention provides an azeotropic or azeotrope-like composition consisting essentially of from about 65 to about 57 mole % HF and from about 35 to about 43 mole % CFC-114a, said composition having a boiling point of from about −25 deg C. at 6.8 psia to about 100 deg C. at 365 psia.

Figure 13:
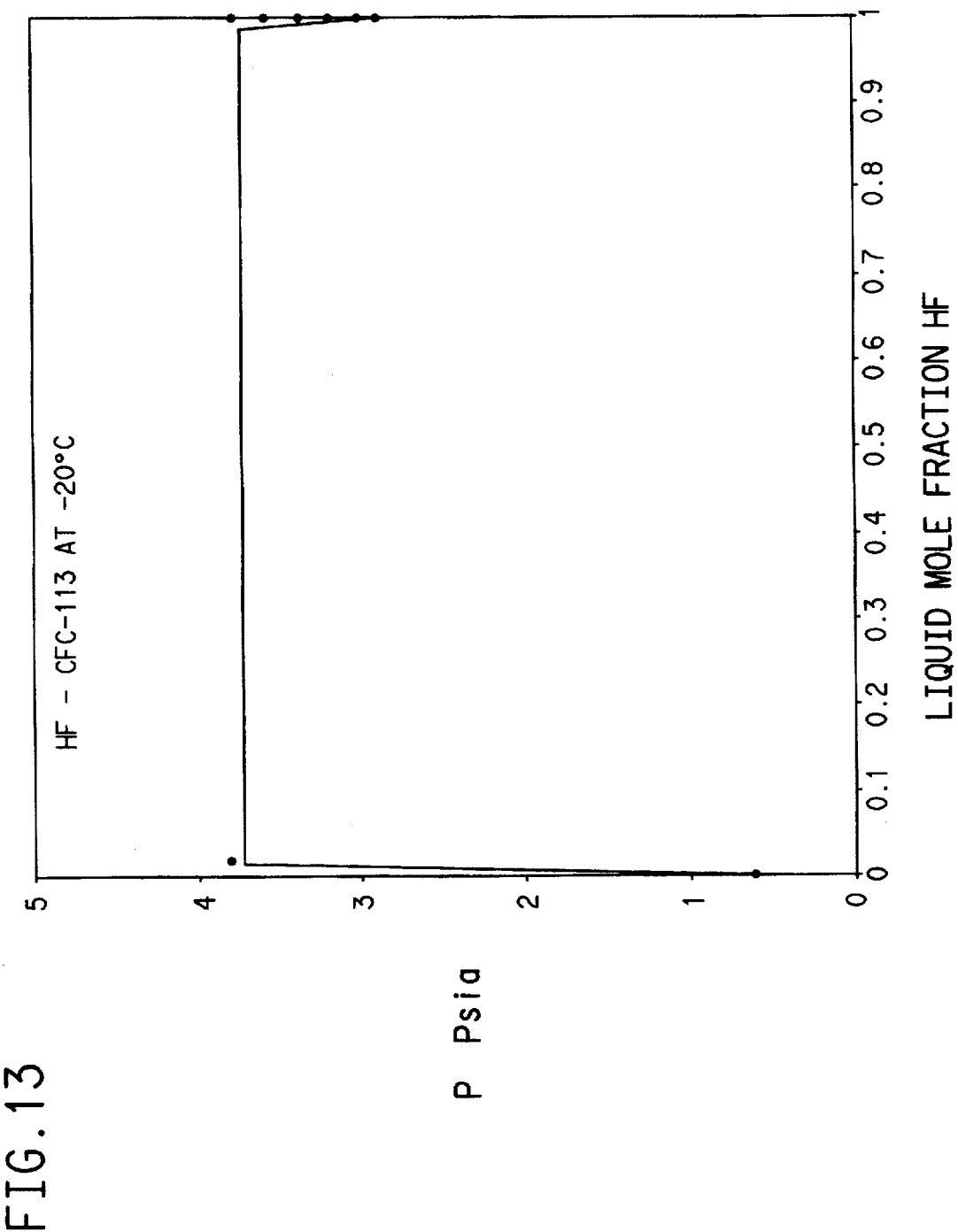
FIG. 13—FIG. 13 is a graphical representation of an azeotropic and azeotrope-like compositions consisting essentially of CFC-113 and HF at a temperature of about −20 deg C.

Referring now to FIG. 13, FIG. 13 illustrates graphically the formation of an azeotropic and azeotrope-like composition consisting essentially of HF and CFC-113 at −20 deg C., as indicated by specific molar mixtures of HF and CFC-113 having a higher vapor pressure than either pure component at this temperature, with the composition of the vapor space in the maximum pressure region being that of the azeotrope. Sampling of the vapor space and NRTL calculations show that the azeotropic or azeotrope-like composition was about 93 mole % HF and 7 mole % CFC-113 at this temperature. Based upon these findings, it has been calculated that an azeotropic or azeotrope-like compositions of about 94 mole % HF and 6 mole % CFC-113 is formed at −25 deg C. and 3 psia and an azeotropic or azeotrope-like composition of about 73 mole % HF and 27 mole % CFC-113 is formed at 125 deg C. and 441 psia. Accordingly, the present invention provides an azeotropic or azeotrope-like composition consisting essentially of from about 73 to about 94 mole % HF and from about 27 to about 6 mole % CFC-113, said composition having a boiling point of from about −25 deg C. at 3 psia to about 125 deg C. at 441 psia.

Figure 14:
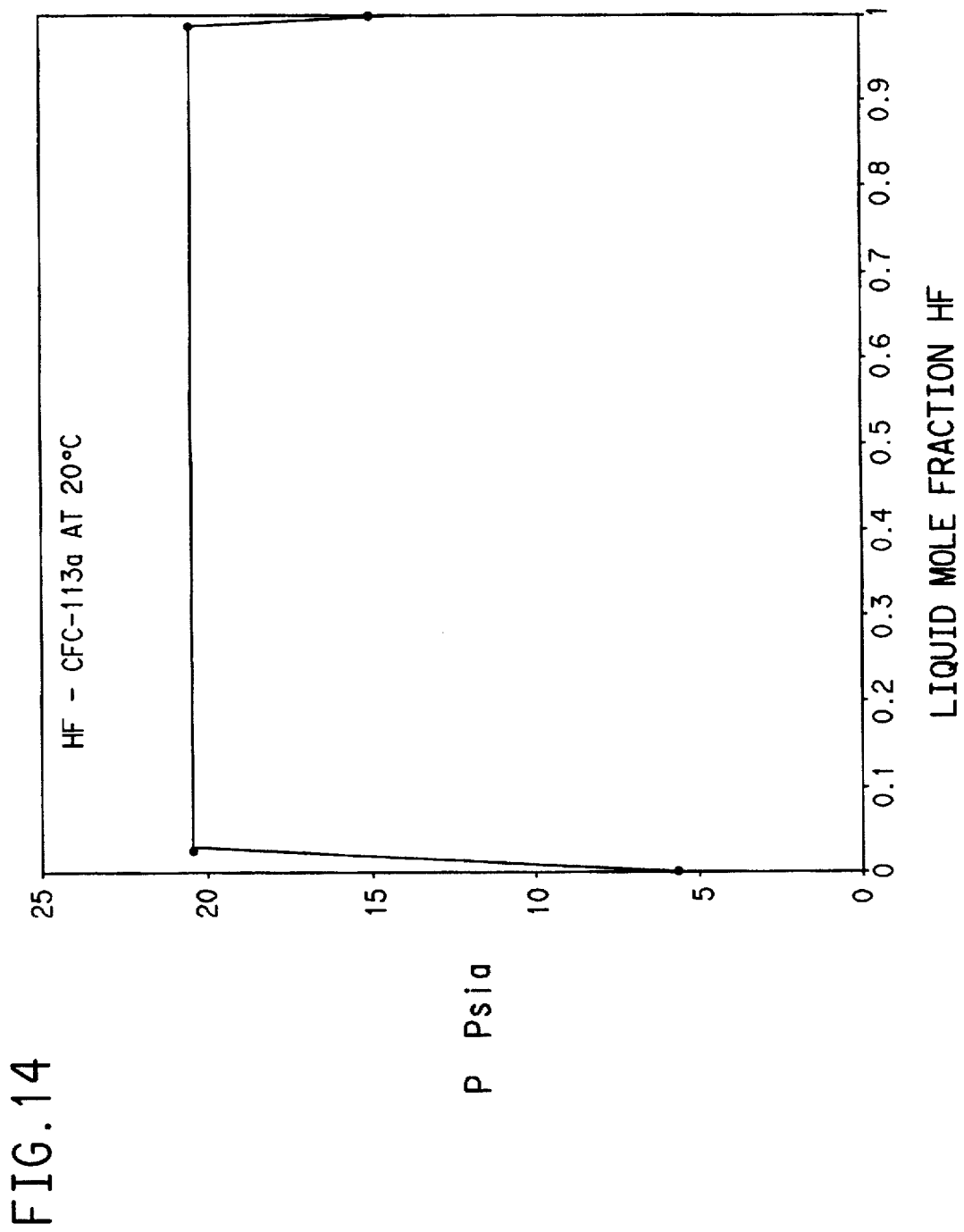
FIG. 14—FIG. 14 is a graphical representation of an azeotropic and azeotrope-like compositions consisting essentially of CFC-113a and HF at a temperature of about 20 deg C.

Referring now to FIG. 14, FIG. 14 illustrates graphically the formation of an azeotropic and azeotrope-like composition consisting essentially of HF and CFC-113a at 20 deg C., as indicated by specific molar mixtures of HF and CFC-113a having a higher vapor pressure than either pure component at this temperature, with the composition of the vapor space in the maximum pressure region being that of the azeotrope. Sampling of the vapor space and NRTL calculations show that the azeotropic or azeotrope-like composition was about 89 mole % HF and 11 mole CFC-113a at this temperature. Based upon these findings, it has been calculated that an azeotropic or azeotrope-like compositions of about 94 mole % HF and 6 mole % CFC-113a is formed at −25 deg C. and 3 psia and an azeotropic or azeotrope-like composition of about 70 mole % HF and 30 mole % PFC-113a is formed at 125 deg C. and 455 psia. Accordingly, the present invention provides an azeotropic or azeotrope-like composition consisting essentially of from about 94 to about 70 mole % HF and from about 6 to about 30 mole % CFC-113a, said composition having a boiling point of from −25 deg C. at 3 psia to about 125 deg C. at 455 psia.

Figure 15:
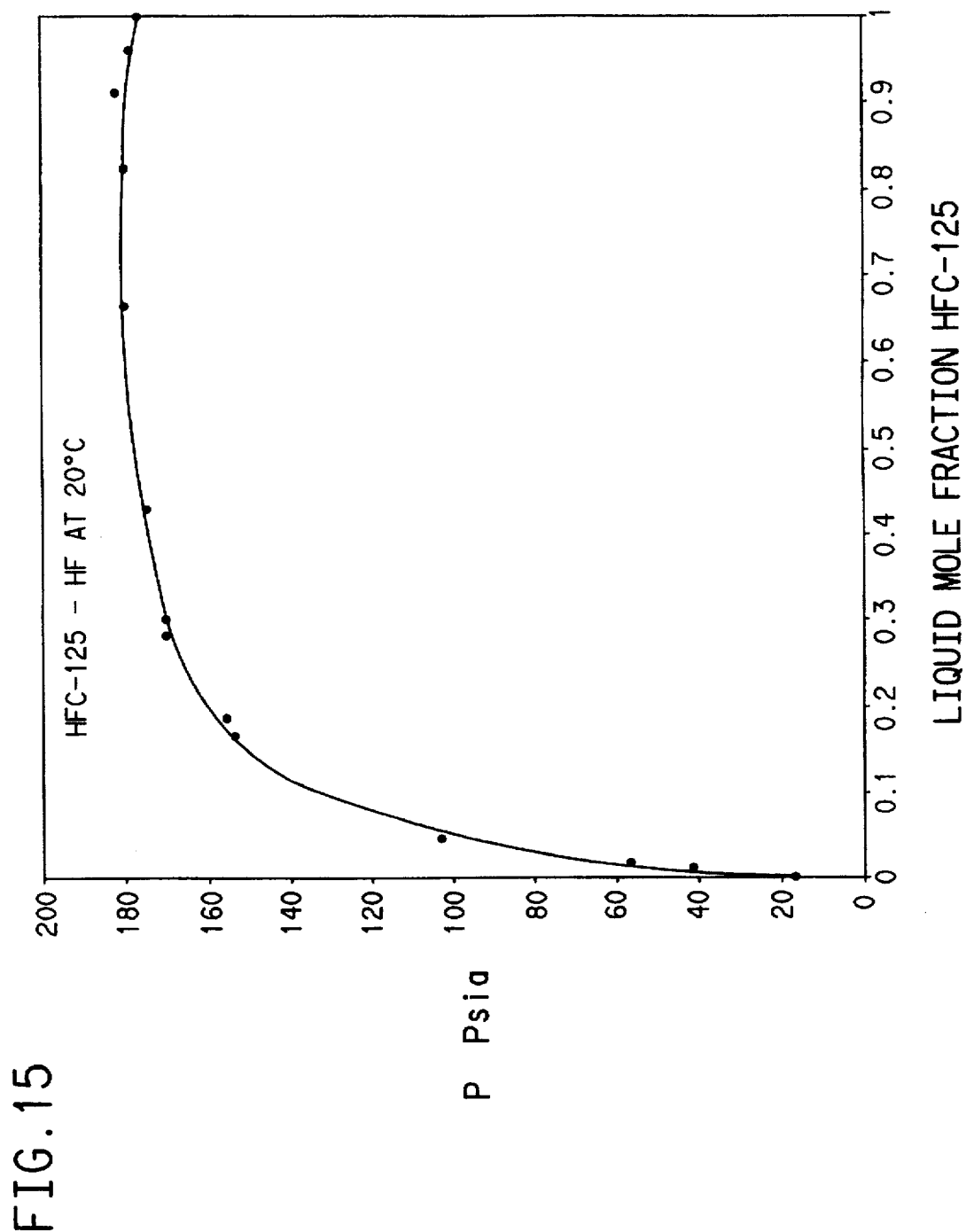
FIG. 15—FIG. 15 is a graphical representation of an azeotropic and azeotrope-like compositions consisting essentially of HFC-125 and HF at a temperature of about 20 deg C.

Referring now to FIG. 15, FIG. 15 illustrates graphically the formation of an azeotropic and azeotrope-like composition consisting essentially of HF and HFC-125 at 20 deg C., as indicated by a mixture of about 14 liquid mole % HF and 86 mole % HFC-125 having the highest pressure over the range of compositions at this temperature. Based upon these findings, it has been calculated that an azeotropic or azeotrope-like compositions of about 11 mole % HF and 89 mole % PFC-125 is formed at −50 deg C. and 13.4 psia and an azeotropic or azeotrope-like composition of about 15 mole % HF and 85 mole % HFC-125 is formed at 50 deg C. and 388 psia. Accordingly, the present invention provides an azeotropic or azeotrope-like composition consisting essentially of from about 14 to about 15 mole % HF and from about 86 to about 85 mole % HFC-125, said composition having a boiling point of from about −50 deg C. at 13.4 psia to about 50 deg C. at 388 psia.

Figure 16:
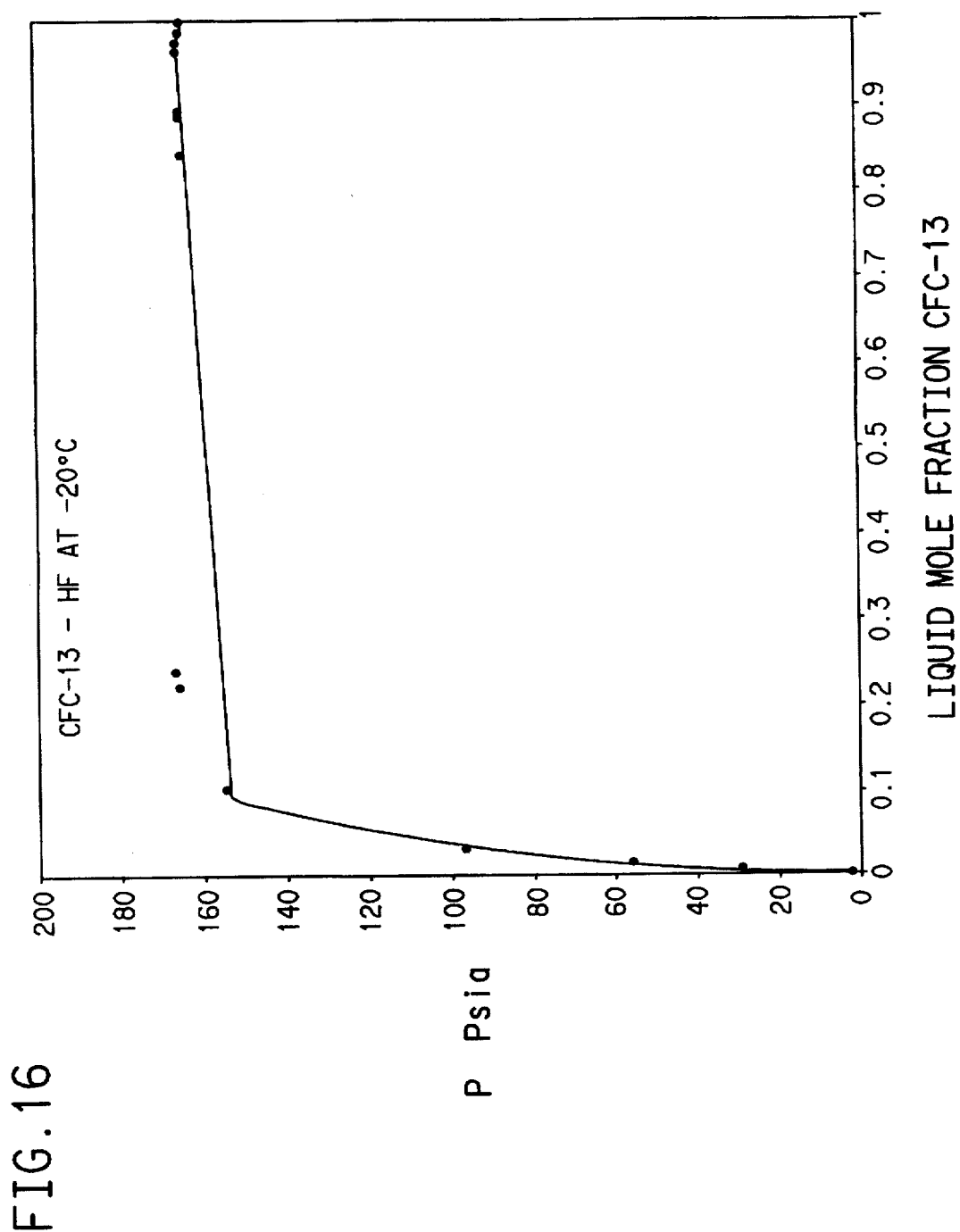
FIG. 16—FIG. 16 is a graphic representation of azeotropic and azeotrope-like compositions consisting essentially of CFC-13 and HF at a temperature of about −20 deg C.

Referring now to FIG. 16, FIG. 16 illustrates graphically the formation of an azeotropic and azeotrope-like composition consisting essentially of HF and CFC-13 at −20 deg C., as indicated by a mixture of about 6 mole % HF and 94 mole % CFC-13 having the highest pressure over the range of compositions at this temperature. Based upon these findings, it has been calculated that an azeotropic or azeotrope-like compositions of about 3 mole % HF and 97 mole % CFC-13 is formed at −50 deg C. and 60 psia and an azeotropic or azeotrope-like composition of about 11 mole % HF and 89 mole % CFC-13 is formed at 25 deg C. and 521 psia. Accordingly, the present invention provides an azeotropic or azeotrope-like composition consisting essentially of from about 3 to about 11 mole HF and from about 97 to about 89 mole % CFC-13, said composition having a boiling point of from about −50 deg C. at 60 psia to about 25 deg C. at 521 psia.

Figure 17:
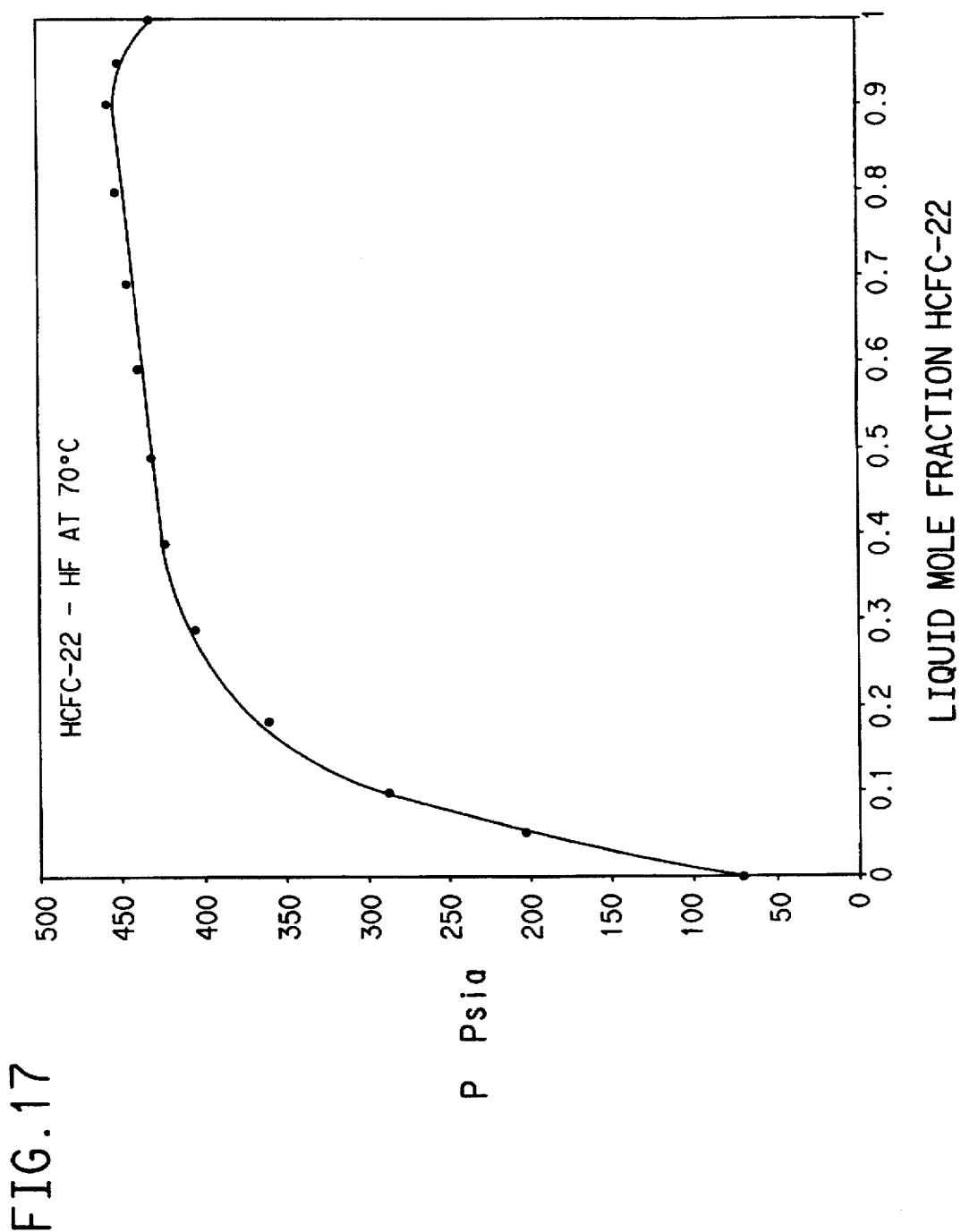
FIG. 17—FIG. 17 is a graphic representation of azeotropic and azeotrope-like compositions consisting essentially of HCFC-22 and HF at a temperature of about 70 deg C.

Referring now to FIG. 17, FIG. 17 illustrates graphically the formation of an azeotropic and azeotrope-like composition consisting essentially of HF and HCFC-22 at 70 deg C., as indicated by a mixture of about 9.9 mole % HF and 90.1 mole % HCFC-22 having the highest vapor pressure over the range of compositions at that temperature. Based upon these findings, it has been calculated that an azeotropic or azeotrope-like compositions of about 14 mole % HF and 86 mole % HCFC-22 is formed at −50 deg C. and 10 psia and an azeotropic or azeotrope-like composition of about 10 mole % HF and 90 mole % HCFC-22 is formed at 70 deg C. and 458 psia. Accordingly, the present invention provides an azeotropic or azeotrope-like composition consisting essentially of from about 14 to about 10 mole % HF and from about 86 to about 90 mole % HCFC-22, said composition having a boiling point of from about −50 deg C. at 10 psia to about 70 deg C. at 458 psia.

Figure 18:
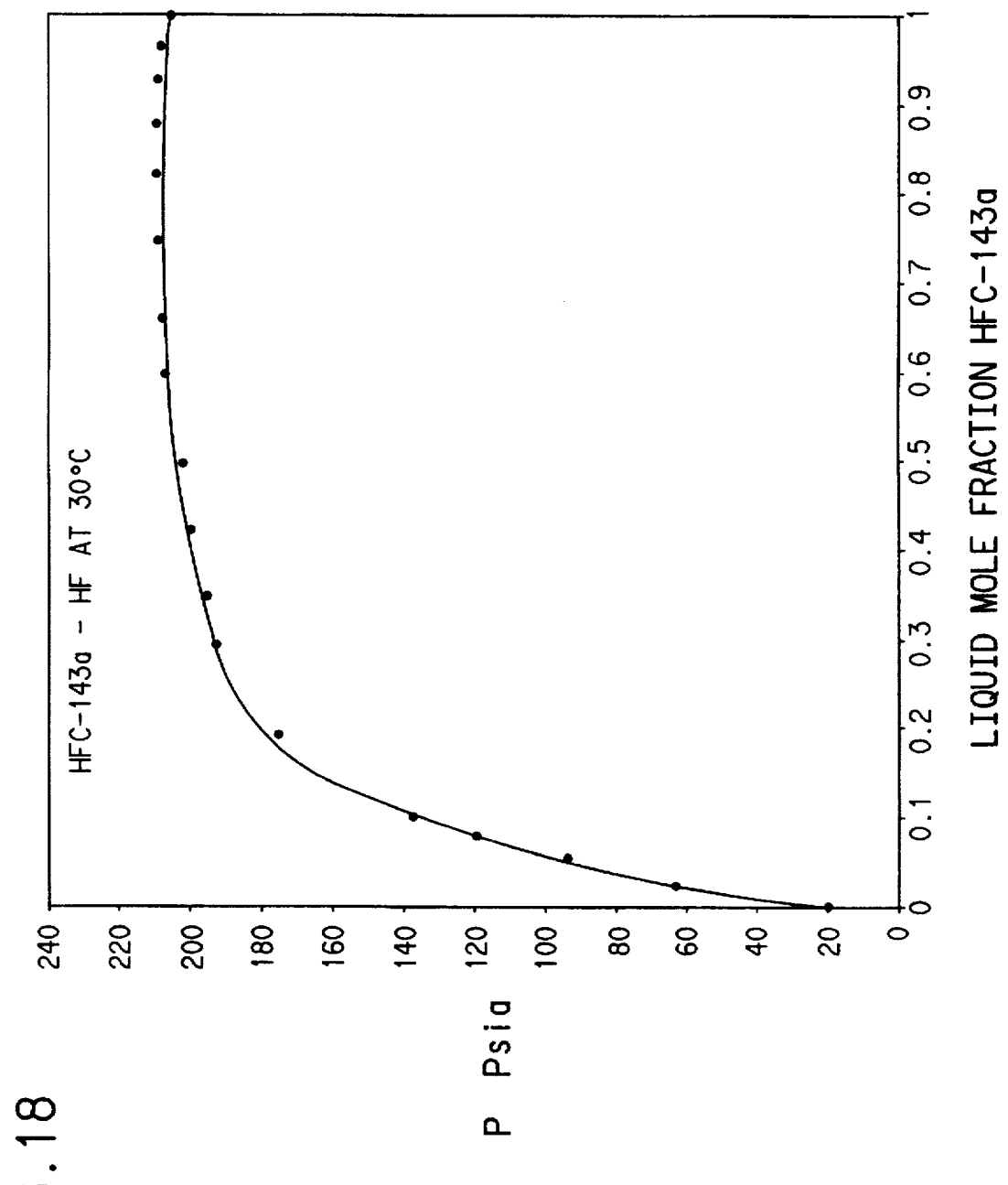
FIG. 18—FIG. 18 is a graphic representation of azeotropic and azeotrope-like compositions consisting essentially of HFC-143a and HF at a temperature of about 30 deg C.

Referring now to FIG. 18, FIG. 18 illustrates graphically the formation of an azeotropic and azeotrope-like composition consisting essentially of HF and HFC-143a at 0 deg C., as indicated by a mixture of about 12.6 mole % HF and 77.4 mole % HFC-143a having the highest pressure over the range of compositions at this temperature. Based upon these findings, it has been calculated that an azeotropic or azeotrope-like compositions of about 13.8 mole % HF and 86.2 mole % PFC-143a is formed at −25 deg C. and 38.7 psia and an azeotropic or azeotrope-like composition of about 5 mole % HF and 95 mole % HFC-143a is formed at 70 deg C. and 595 psia. Accordingly, the present invention provides an azeotropic or azeotrope-like composition consisting essentially of from about 13.8 to about 5 mole % HF and from about 86.2 to about 95 mole % HFC-143a, said composition having a boiling point of from about −25 deg C. at 38.7 psia to about 70 deg C. at 595 psia.

The followed is claimed:

1. An azeotropic composition consisting essentially of about 95 to about 85 mole percent hexafluoroethane and about 4 to about 15 mole percent hydrogen fluoride, said composition having a boiling point from about −50 degrees C. at 54 psia to about 8 degrees C. at 343 psia.

2. An azeotropic composition consisting essentially of about 97 to about 89 mole percent chlorotrifluoroethane and about 3 to about 11 mole percent hydrogen fluoride, said composition having a boiling point from about −50 degrees C. at 60 psia to about 25 degrees C. at 343 psia.

3. A liquefied azeotropic composition consisting essentially of hexafluoroethane or chlorotrifluoromethane in combination with an effective amount of hydrogen fluoride to form said composition.

4. An azeotropic composition consisting essentially of i) hexafluoroethane in combination with an effective amount of hydrogen fluoride to form said composition wherein said composition has a boiling point from about −50 degrees C. at about 54 psia to about 8 degrees C. at about 343 psia, or ii) chlorotrifluoromethane in combination with an effective amount of hydrogen fluoride to form said composition wherein said composition has a boiling point from about −50 degrees C. at about 60 psia to about 25 degrees C. at about 521 psia.

5. A composition consisting essentially of hexafluoroethane or chlorotrifluoromethane and hydrogen fluoride wherein said composition has a boiling point from about −50 degrees C. at about 54 psia to about 8 degrees C. at about 343 psia, or from about −50 degrees C. at about 60 psia to about 25 degrees C. at about 521 psia.

6. The composition of claim 4 or 5 wherein the amount of hydrogen fluoride is from about 3 to about 15 mole percent.

7. The composition of claim 4 or 5 wherein the vapor pressure of the composition is greater than the vapor pressure of either pure hexafluoroethane or hydrogen fluoride, or of either chlorotrifluoromethane or hydrogen fluoride.

* * * * *